(12) United States Patent
Ankersmit et al.

(10) Patent No.: US 11,333,662 B2
(45) Date of Patent: May 17, 2022

(54) POTENCY ASSAY OF SECRETOMES

(71) Applicant: APOSCIENCE AG, Vienna (AT)

(72) Inventors: Hendrik Jan Ankersmit, Vienna (AT); Michael Mildner, Neulengbach (AT)

(73) Assignee: APOSCIENCE AG, Vienna (AT)

( * ) Notice: Subject to any disclaimer, the term of this patent is extended or adjusted under 35 U.S.C. 154(b) by 204 days.

(21) Appl. No.: 16/763,813

(22) PCT Filed: Dec. 19, 2018

(86) PCT No.: PCT/EP2018/085955
§ 371 (c)(1),
(2) Date: May 13, 2020

(87) PCT Pub. No.: WO2019/121989
PCT Pub. Date: Jun. 27, 2019

(65) Prior Publication Data
US 2020/0386740 A1    Dec. 10, 2020

(30) Foreign Application Priority Data
Dec. 20, 2017  (EP) ..................................... 17209165

(51) Int. Cl.
*G01N 33/50*   (2006.01)
*C12Q 1/66*    (2006.01)

(52) U.S. Cl.
CPC ........... *G01N 33/5023* (2013.01); *C12Q 1/66* (2013.01)

(58) Field of Classification Search
CPC .............................. G01N 33/5023; C12Q 1/66
USPC .......................................................... 435/8
See application file for complete search history.

(56) References Cited

U.S. PATENT DOCUMENTS

2011/0250190 A1* 10/2011 Ankersmit ................ A61P 9/10
424/93.71
2012/0045418 A1*  2/2012 Ankersmit .............. A61P 41/00
424/93.7
2015/0352092 A1  12/2015 Hockerman
2016/0256444 A1   9/2016 Yan

FOREIGN PATENT DOCUMENTS

EP         2044935        4/2009

OTHER PUBLICATIONS

Hoetzenecker et al., Mononuclear cell secretome protects from experimental autoimmune myocarditis, European Heart Journal, vol. 36, (2015), pp. 676-685.*
Hoetzenecker K et al., "Secretome of apoptotic peripheral blood cells (APOSEC) attenuates microvascular obstruction in a porcine closed chest reperfused acute myocardial infraction model: role of platelet aggregation and vasodilation", Basic Research in Cardiology, Steinkopff-Verlag, DA, vol. 107, No. 5, Aug. 17, 2012.
Lichtenauer Michael et al., "Secretome of apoptotic peripheral blood cells (APOSEC) confers cytoprotection to cardiomyocytes and inhibits tissue remodeling after acute myocardial infarction: a preclinical study", Basic Research in Cardiology Nov. 2011, vol. 106, No. 6, Nov. 2011.
Beer Lucian et al., "Peripheral blood mononuclear cell secretome fortissue repair", Apoptosis, London, GB, vol. 21, No. 12, Oct. 1, 2016.
International Search Report issued in PCT/EP2018/085955 dated Jan. 24, 2019.

* cited by examiner

*Primary Examiner* — Jennifer M. H. Tichy
(74) *Attorney, Agent, or Firm* — Workman Nydegger

(57) ABSTRACT

The present invention relates to a method for determining the potency of a supernatant of a mammalian cell culture to be used in the treatment of an inflammatory condition.

20 Claims, 26 Drawing Sheets

| Cell Type | HEK293 | | | | | | A549 | | | | | | HaCat | | | | | |
|---|---|---|---|---|---|---|---|---|---|---|---|---|---|---|---|---|---|---|
| Cell Number / well | 20'000 | | | 80'000 | | | 20'000 | | | 80'000 | | | 20'000 | | | 80'000 | | |

Firefly counts

| | ratio | 1 | 2 | 3 | 4 | 5 | 6 | 7 | 8 | 9 | 10 | 11 | 12 |
|---|---|---|---|---|---|---|---|---|---|---|---|---|---|
| A | | 2987 | 7730 | 22906 | 18194 | 2473 | 758 | 843 | 678 | 238 | 129 | 116 | 91 |
| B | 7.5 | 311'717 | 324'906 | 2'855'133 | 2'881'628 | 16'785 | 5'338 | 99'838 | 71'778 | 862 | 362 | 349 | 322 |
| Attractene C | 3.75 | 553'156 | 453'115 | 1'798'790 | 2'013'333 | 84'731 | 82'838 | 134'948 | 125'786 | 32'218 | 23'400 | 4'065 | 5'350 |
| D | 1.875 | 359'097 | 344'738 | 1'849'024 | 1'996'005 | 117'036 | 141'915 | 105'302 | 106'445 | 33'174 | 37'982 | 3'299 | 3'242 |
| E | 1.125 | 9'801 | 14'169 | 21'444 | 32'036 | 4'461 | 3'087 | 4'930 | 5'982 | 1'674 | 935 | 150 | 113 |
| Fugene F | 2.25 | 632'399 | 771'831 | 790'592 | 1'596'431 | 47'619 | 38'180 | 400'994 | 461'994 | 29'132 | 26'074 | 1'110 | 1'383 |
| G | 4.5 | 5'914'098 | 5'436'489 | 6'382'266 | 7'728'022 | 1'644'334 | 1'340'390 | 5'386'750 | 5'255'568 | 107'891 | 98'499 | 5'583 | 4'007 |
| H | | 17837 | 23401 | 30525 | 33807 | 10140 | 9893 | 22270 | 23010 | 1650 | 865 | 154 | 90 |

Renilla counts

| | ratio | 1 | 2 | 3 | 4 | 5 | 6 | 7 | 8 | 9 | 10 | 11 | 12 |
|---|---|---|---|---|---|---|---|---|---|---|---|---|---|
| A | | 2365 | 4110 | 7341 | 10290 | 1395 | 713 | 904 | 1036 | 327 | 243 | 204 | 195 |
| B | 7.5 | 232'578 | 158'634 | 1'128'493 | 1'324'141 | 18'949 | 11'166 | 121'916 | 107'203 | 770 | 556 | 542 | 357 |
| Attractene C | 3.75 | 403'670 | 262'474 | 1'052'978 | 1'250'387 | 268'901 | 269'780 | 250'288 | 223'774 | 16'852 | 14'177 | 3'738 | 3'510 |
| D | 1.875 | 267'222 | 257'671 | 1'075'984 | 1'103'121 | 590'326 | 705'644 | 245'878 | 243'537 | 23'476 | 28'929 | 2'608 | 2'360 |
| E | 1.125 | 5'280 | 4'866 | 14'038 | 16'776 | 6'443 | 4'590 | 6'431 | 6'481 | 842 | 742 | 214 | 201 |
| Fugene F | 2.25 | 256'590 | 281'257 | 544'304 | 949'946 | 57'506 | 44'124 | 395'817 | 504'893 | 6'322 | 9'094 | 710 | 636 |
| G | 4.5 | 2'099'243 | 1'831'728 | 2'845'713 | 3'610'724 | 1'290'346 | 1'263'930 | 3'603'506 | 3'368'982 | 32'882 | 26'268 | 1'885 | 1'890 |
| H | | 5108 | 6787 | 11794 | 13568 | 6246 | 6890 | 12938 | 12514 | 942 | 451 | 210 | 190 |

Fig. 11

POTENCY ASSAY OF SECRETOMES

TECHNICAL FIELD

The present invention relates to potency assays to be used in testing the capability of a composition to be used in the treatment of inflammatory conditions.

BACKGROUND ART

Legislation in many jurisdictions requires that pharmaceutical preparations containing a plurality of active compounds, whose exact composition may even not entirely be known, are to be evaluated for their potency before released onto the market. Usually each batch produced has to be evaluated for its potency using respective potency assays.

Potency assays can be used to show that a specific product has biologic activities relevant for treating diseases or disorders. It is not a requirement of potency assays to reflect all of the product's biologic functions, but it should indicate one or more relevant biologic functions. There is a strong need to identify those parameters that are critical to the efficacy of therapeutic products and to control them (e.g. via potency testing) such that products of consistent quality can be manufactured. A major advantage of potency assays is the fact that with the identification and/or quantification of a small number of "reporter" proteins or enzyme activities (e.g. 2, 3, 4, or 5, ideally only 1) within complex pharmaceutical preparations the therapeutic suitability of said preparation can be determined.

Cells, in particular mammalian cells, are known to secrete numerous substances during cultivation into a cell culture medium. The so obtained conditioned culture media can be used in the treatment and/or prevention of diseases and disorders. For instance, WO 2010/070105 and WO 2010/079086 disclose conditioned culture media ("supernatants") which are obtained by cultivation of peripheral blood mononuclear cells (PBMCs) and which can be used in the treatment of various inflammatory conditions.

SUMMARY OF INVENTION

Cell-free or cell-containing conditioned culture medium obtainable by cultivating PBMCs subjected before or during cultivation to stress inducing conditions turned out to be effective in the treatment of various diseases associated i.a. with inflammation (see WO 2010/070105 and WO 2010/079086). Since such a conditioned culture medium comprises i.a. a plurality of substances secreted or released by PBMCs which may have an influence on the biological activity of the conditioned medium it is of importance to have an assay which indicates whether said medium has the desired activity.

It is therefore an object of the present invention to provide an assay which allows determining whether a conditioned culture medium obtainable by the cultivation of PBMCs has an activity for treating diseases and disorders associated with inflammation. Such an assay is useful for demonstrating consistent potency among different production lots of the conditioned culture medium acceptable for pharmaceutical use.

The inventors found a potency assay to measure the biological activity and therapeutic efficacy of conditioned culture media by monitoring the expression of specific proteins and/or the regulation of certain promoters. It turned surprisingly out that a conditioned culture medium obtainable by the cultivation of PBMCs and having the capacity to treat diseases and disorders associated with inflammation is able to induce the expression of phosphorylated heat shock protein 27 (HSP27) in eukaryotic cells when these cells are incubated in said conditioned culture medium. Furthermore the conditioned culture medium activates at least one promoter selected from the group consisting of activator protein 1 (AP-1) promoter, nuclear factor kappa-light-chain-enhancer of activated B cells (NF-κB) promoter, sex determining region Y-box 2 (Sox2) promoter, signal transducer and activator of transcription 3 (STAT3) promoter, early growth response protein 1 (EGR-1) promoter and serum response element (SRE) promoter in eukaryotic cells. Thus, the increased expression of phosphorylated HSP27 and the activation of the AP-1, NF-κB, Sox2, STAT3, EGR-1 and/or SRE promoters indicates that a conditioned culture medium obtainable by the cultivation of PBMCs can be used in the treatment of diseases and disorders associated with inflammation.

Therefore, the present invention relates to a method for determining the potency of a supernatant of a mammalian cell culture to be used in the treatment of an inflammatory condition comprising the steps of
  a) incubating eukaryotic cells in a culture medium comprising or consisting of said supernatant,
  b) measuring a promoter activity of at least one promoter selected from the group consisting of activator protein 1 (AP-1) promoter, nuclear factor kappa-light-chain-enhancer of activated B cells (NF-κB) promoter, sex determining region Y-box 2 (Sox2) promoter, signal transducer and activator of transcription 3 (STAT3) promoter, early growth response protein 1 (EGR-1) promoter and serum response element (SRE) promoter and/or measuring the amount of phosphorylated heat shock protein 27 (HSP27) released by the eukaryotic cells into the culture medium of step a),
  wherein the supernatant of the mammalian cell culture has the potential to be used in the treatment of an inflammatory condition, if the promoter activity of the at least one promoter is at least 50% higher compared to the promoter activity measured when the eukaryotic cells are cultivated in a culture medium lacking said supernatant and/or if the amount of phosphorylated HSP27 released into the culture medium of step a) is at least 20% higher compared to the amount of phosphorylated HSP27 released into the culture medium when the eukaryotic cells are cultivated in a culture medium lacking said supernatant.

A method for determining the potency of a supernatant of a mammalian cell culture to be used in the treatment of an inflammatory condition comprising the steps of
  a) incubating eukaryotic cells in a culture medium comprising or consisting of said supernatant,
  b) measuring a promoter activity of at least one promoter selected from the group consisting of activator protein 1 (AP-1) promoter, nuclear factor kappa-light-chain-enhancer of activated B cells (NF-κB) promoter, sex determining region Y-box 2 (Sox2) promoter, signal transducer and activator of transcription 3 (STAT3) promoter, early growth response protein 1 (EGR-1) promoter and serum response element (SRE) promoter and/or measuring the amount of phosphorylated heat shock protein 27 (HSP27) released by the eukaryotic cells into the culture medium of step a),
  wherein the supernatant of the mammalian cell culture has the potential to be used in the treatment of an inflammatory condition, if the promoter activity of the at least one promoter is up to 25% higher or lower compared to the promoter activity measured when the eukaryotic cells are cultivated in a culture medium comprising a reference supernatant of mammalian cells, which can be used in the treatment of an inflammatory condition and/or if the amount of phosphorylated HSP27 released into the culture medium of step a) is up to 25% higher or lower compared to the amount of phosphorylated HSP27 released into the culture medium of step a) comprising a reference supernatant of mammalian cells, which can be used in the treatment of an inflammatory condition.

In an embodiment of the present invention the supernatant of a mammalian cell culture is a supernatant of a peripheral blood mononuclear cell (PBMC) culture.

In another embodiment of the present invention the mammalian cell culture comprises T cells, B cells and/or NK cells.

In a further embodiment of the present invention the mammalian cells in the mammalian cell culture are cultivated in a cell culture medium selected from the group consisting of a cell growth medium, preferably CellGro medium (CellGenix, Freiburg, Germany), more preferably Cellgro GMP DC medium (also known as "CellGenix GMP DC medium"; CellGenix, Freiburg, Germany), RPMI, DMEM, X-vivo and Ultraculture.

In an embodiment of the present invention the mammalian cells are subjected to one or more stress inducing conditions before or during cultivation.

In another embodiment of the present invention the stress inducing condition is selected from the group consisting of radiation, in particular ionizing radiation or UV radiation, hypoxia, ozone, heat, osmotic pressure and pH shift.

In an embodiment of the present invention the mammalian cells are subjected to an ionizing radiation at a dose of at least 10 Gy, preferably at least 20 Gy, more preferably at least 40 Gy.

In a further embodiment of the present invention the mammalian cells are cultivated for at least 4 h, preferably for at least 6 h, more preferably for at least 12 h, before isolating its supernatant.

In an embodiment of the present invention the inflammatory condition is a condition associated with ischemia, preferably a skin condition or an internal inflammatory condition.

In a further embodiment of the present invention the skin condition is selected from the group consisting of wounds, tissue ischemia, chronic wounds, diabetic wounds, skin ulcer, skin burns, skin flaps in plastic surgery and tissue regeneration after dental grafting.

In an embodiment of the present invention the internal inflammatory condition is selected from the group consisting of myocardial ischemia, limb ischemia, tissue ischemia, ischemia reperfusion injury, angina pectoris, coronary artery disease, peripheral vascular disease, peripheral arterial disease, stroke, ischemic stroke, myocardial infarct, congestive heart failure, trauma, bowel disease, mesenterial infarction, pulmonary infarction, bone fracture, tissue regeneration after dental grafting, auto-immune diseases, rheumatic diseases, transplantation allograft and rejection of allograft.

In another embodiment of the present invention the eukaryotic cells of step a) are selected from the group consisting of adenocarcinomic human alveolar basal epithelial cells, preferably A549 cells, aneuploid immortal keratinocyte cells (HaCaT), human embryonic kidney cells (HEK cells), preferably HEK293 cells, and neuroblastoma cells, preferably SH-SY5Y cells.

In a further embodiment of the present invention the eukaryotic cells of step a) are incubated in the cell culture medium for at least 2 hours, preferably at least 4 hours, more preferably at least 6 hours, more preferably at least 12 hours, more preferably at least 18 hours, more preferably at least 24 hours.

In an embodiment of the present invention the culture medium comprises at least 20%, preferably at least 50%, more preferably at least 70%, more preferably at least 80%, more preferably at least 90%, more preferably at least 95%, of said supernatant.

In another embodiment of the present invention the culture medium of step a) is a Dulbecco's Modified Eagle Medium (DMEM), a Ham's F12 Medium (F12), a minimum essential medium or a combination of one or more of these media.

In an embodiment of the present invention the culture medium of step a) comprises 2 to 20%, preferably 5 to 15%, fetal bovine serum (FBS) and/or L-alanyl-L-glutamine.

In a further embodiment of the present invention the eukaryotic cells comprise at least one expression cassette comprising a promoter selected from the group consisting of an AP-1 promoter, NF-κB promoter, Sox2 promoter, STAT3 promoter, EGR-1 promoter and SRE promoter operably linked to at least one nucleic acid molecule encoding for a reporter protein.

In an embodiment of the present invention the reporter protein is selected from the group consisting of a luciferase, preferably a firefly luciferase, and a fluorescent protein, preferably a green fluorescent protein.

In another embodiment of the present invention the amount of the protein released by the cells into the culture medium is determined by an immunological method, preferably by enzyme-linked immunosorbent assay (ELISA), by a photometrical method or by a fluorescent method.

In an embodiment of the present invention the eukaryotic cells of step a) are adenocarcinomic human alveolar basal epithelial cells, preferably A549 cells, HaCaT or HEK cells, preferably HEK293 cells, and the amount of phosphorylated HSP27 is determined.

In a further embodiment of the present invention the promoter activity of the at least one promoter is at least 80%, preferably at least 100%, more preferably at least 150%, more preferably at least 200%, higher compared to the promoter activity measured when the eukaryotic cells are cultivated in a culture medium lacking said supernatant.

In an embodiment of the present invention the eukaryotic cells of step a) are adenocarcinomic human alveolar basal epithelial cells, preferably A549 cells, HaCaT cells or HEK cells, preferably HEK293 cells, when the amount of phosphorylated HSP27 released into the culture medium is measured.

In another embodiment of the present invention the eukaryotic cells of step a) are neuroblastoma cells, preferably SH-SY5Y cells, or HaCaT cells comprising at least one expression cassette comprising an AP-1 promoter operably linked to at least one nucleic acid molecule encoding for a reporter protein.

In an embodiment of the present invention the eukaryotic cells of step a) are adenocarcinomic human alveolar basal epithelial cells, preferably A549 cells, comprising at least one expression cassette comprising an NF-κB or Sox2 promoter operably linked to at least one nucleic acid molecule encoding for a reporter protein.

In a further embodiment of the present invention the eukaryotic cells of step a) are HEK cells, preferably HEK293 cells, comprising at least one expression cassette comprising an EGR-1, SRE, AP-1 or STAT3 promoter operably linked to at least one nucleic acid molecule encoding for a reporter protein.

BRIEF DESCRIPTION OF THE FIGURES

FIG. 11 shows a Table summarizing the results of the transfection efficacy test of example 7.

DESCRIPTION OF EMBODIMENTS

Figure 1A:
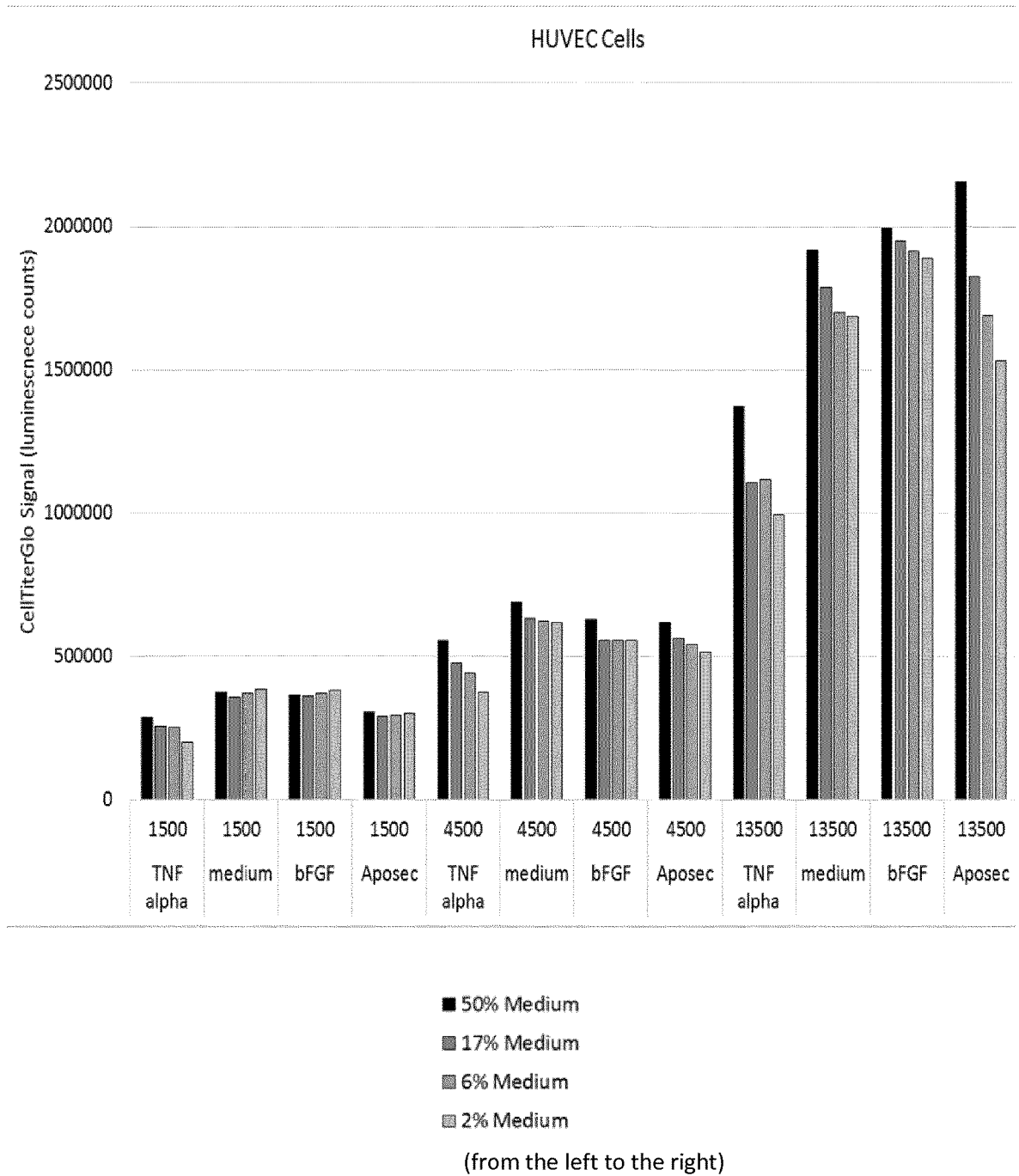
FIG. 1 shows the results of the proliferation assay (example 1). The graphs indicate the cell numbers upon overnight proliferation (CellTiter-Glo signal). A. HUVEC cells; B: NHDF cells; C: A549 cells.

The present invention relates to a method for determining the potency of a supernatant of a mammalian cell culture to be used in the treatment of inflammatory conditions.

"Potency", as used herein, is defined to be the biological activity of a composition (e.g. supernatant of a cell culture) required in the treatment or prevention of diseases, disorders or conditions, in particular those diseases, disorders or conditions which involve inflammation.

"Potency assay", as used herein, refers to a method for determining the potency of a composition. The potency assay measures directly or indirectly the presence or the amount of a specific substance or a specific composition of substances in a sample, i.e. in a supernatant of a mammalian cell culture. The presence or the amount of a specific substance or a specific composition of substances in the sample indicates whether the supernatant can be used in the treatment of an inflammatory condition. Therefore, a supernatant known to be effective in the treatment of an inflammatory condition can be used as a reference. In such a case the promoter activity of at least one promoter selected from the group consisting of activator protein 1 (AP-1) promoter, nuclear factor kappa-light-chain-enhancer of activated B cells (NF-κB) promoter, sex determining region Y-box 2 (Sox2) promoter, signal transducer and activator of transcription 3 (STAT3) promoter, early growth response protein 1 (EGR-1) promoter and serum response element (SRE) promoter and/or the amount of phosphorylated heat shock protein 27 (HSP27) released by the eukaryotic cells into the culture medium of step a) comprising a sample of an-other batch of a supernatant is measured and then compared with the effect caused by a reference supernatant as defined above. Any promoter activity or protein amount variation in a range of +/−25% (i.e. up to 25% higher or lower), preferably +/−20%, more preferably +/−15%, more preferably +/−10%, more preferably +/−5%, in relation to a reference supernatant indicates that the batch of supernatant can be used in the treatment of an inflammatory condition. The same is valid also for the amount of phosphorylated HSP27.

Therefore, another aspect of the present invention relates to a method for determining the potency of a supernatant of a mammalian cell culture to be used in the treatment of an inflammatory condition comprising the steps of a) incubating eukaryotic cells in a culture medium comprising or consisting of said supernatant, b) measuring a promoter activity of at least one promoter selected from the group consisting of activator protein 1 (AP-1) promoter, nuclear factor kappa-light-chain-enhancer of activated B cells (NF-κB) promoter, sex determining region Y-box 2 (Sox2) promoter, signal transducer and activator of transcription 3 (STAT3) promoter, early growth response protein 1 (EGR-1) promoter and serum response element (SRE) promoter and/or measuring the amount of phosphorylated heat shock protein 27 (HSP27) released by the eukaryotic cells into the culture medium of step a), wherein the supernatant of the mammalian cell culture has the potential to be used in the treatment of an inflammatory condition, if the promoter activity of the at least one promoter is up to 25% higher or lower compared to the promoter activity measured when the eukaryotic cells are cultivated in a culture medium comprising a reference supernatant of mammalian cells, which can be used in the treatment of an inflammatory condition and/or if the amount of phosphorylated HSP27 released in-to the culture medium of step a) is up to 25% higher or lower compared to the amount of phosphorylated HSP27 released into the culture medium of step a) comprising a reference supernatant of mammalian cells, which can be used in the treatment of an inflammatory condition.

"Inflammatory conditions", as used herein, refers to disorders, diseases and conditions associated at least in part with inflammation.

As described above supernatants of mammalian cell cultures are able to influence the protein expression of certain proteins in eukaryotic cells. In addition thereto, these supernatants are also able to regulate (activate or inhibit) the activity of promoters present in eukaryotic cells. Both effects can be used for determining the potency of supernatants of mammalian cell cultures to be used in the treatment of inflammatory conditions.

"Promoter", as used herein, refers to means a nucleic acid stretch typically located upstream a nucleic acid molecule encoding a functional polypeptide or protein. The promoter is functional in host cells and regulates the transcription of nucleic acid stretches found downstream to the promoter. The promoter comprises transcription factor binding sites as well as a transcription initiation region.

It turned out that a supernatant of a mammalian cell culture increases the expression rate of phosphorylated heat shock protein 27 (HSP27) of eukaryotic cells, when the latter cells are incubated with said supernatant. If the eukaryotic cells are human cells human HSP27 (UniProt P04792) may be phosphorylated at least at one position selected from amino acid residues 15, 26, 65, 78, 82, 83, 86, 98, 174, 176 and 199 of HSP27, whereby the preferred phosphorylated amino acid residues are at position 15 and 82 of HSP27.

In order to determine and/or quantify phosphorylated HSP27 in the culture medium according to step b) various methods can be employed. The most preferred methods involve the use of antibodies or antigen binding fragments thereof including Fab fragments or other fragments containing the variable antigen binding regions of such antibodies. These antibodies and fragments can be used in an immunoassay, preferably an enzyme-linked immunosorbent assay (ELISA), to determine phosphorylated HSP27.

The influence of a supernatant of a mammalian cell culture (i.e. conditioned culture medium) on the activity of specific promoters can be tested using various methods. One method involves the measurement of the naturally occurring protein encoded by the nucleic acid which is operably linked to the respective promoter. This can be done using antibodies or functional fragments thereof binding to said protein or by determining the amount of mRNA transcribed and encoding for said protein. Alternatively, the promoters which are influenced by the supernatant of the mammalian cell culture can be operably linked to a nucleic acid molecule encoding a reporter protein using recombinant methods known in the art. Also these reporter proteins may be quantified by using antibodies or antigen-binding fragments thereof in immunoassays. Alternatively, such reporter proteins may have enzymatic activities or fluorescent properties. If the reporter proteins have enzymatic activity assays can be used to determine the amount of substrate converted in order to draw a conclusion on the promoter activity.

According to the present invention preferred promoters are activator protein 1 (AP-1) promoter, nuclear factor kappa-light-chain-enhancer of activated B cells (NF-κB) promoter, sex determining region Y-box 2 (Sox2) promoter, signal transducer and activator of transcription 3 (STAT3) promoter, early growth response protein 1 (EGR-1) promoter and serum response element (SRE) promoter.

It turned out that the supernatant of the mammalian cell culture has the potential to be used in the treatment of an inflammatory condition, if the amount of phosphorylated HSP27 released into the culture medium of step a) is at least 20% higher compared to the amount of phosphorylated HSP27 released into the culture medium when the eukaryotic cells are cultivated in a culture medium lacking said supernatant and/or if the promoter activity of the at least one promoter is at least 50% higher compared to the promoter activity measured when the eukaryotic cells are cultivated in a culture medium lacking said supernatant.

As mentioned above the promoter activity of the promoters is at least 50%, preferably at least 60%, more preferably at least 70%, more preferably at least 80%, more preferably at least 90%, more preferably at least 100%, more preferably at least 150%, more preferably at least 200%, higher compared to the promoter activity measured when the eukaryotic cells are cultivated in a culture medium lacking said supernatant. "Lacking said supernatant" means that eukaryotic cells are incubated in a culture medium lacking the conditioned culture medium (i.e. the supernatant of a mammalian cell culture).

The amount of phosphorylated HSP27 released into the culture medium of step a) is at least 20%, preferably at least 30%, more preferably at least 50%, more preferably at least 70%, more preferably at least 100%, higher compared to the amount of phosphorylated HSP27 released into the culture medium when the eukaryotic cells are cultivated in a culture medium lacking said supernatant.

In another aspect of the present invention a reference supernatant of a mammalian cell culture is used which has already been shown to be able to treat inflammatory conditions. In such a case the promoter activity of the at least one promoter is up to 25% higher or lower compared to the promoter activity measured when the eukaryotic cells are cultivated in a culture medium comprising said reference supernatant and/or if the amount of phosphorylated HSP27 released into the culture medium of step a) is up to 25% higher or lower compared to the amount of phosphorylated HSP27 released into the culture medium of step a) comprising said reference supernatant.

In a first step of the method of the present invention the eukaryotic cells are cultivated/incubated in a culture medium comprising or consisting of a supernatant of a mammalian cell culture. The cultivation conditions are those which are usually used to cultivate the eukaryotic cells in a standard culture medium. Typically the eukaryotic cells are cultivated/incubated at a temperature of 35° C. to 39° C., preferably of 36° C. to 38° C., in particular of approx. 37° C.

In a preferred embodiment of the present invention the supernatant of a mammalian cell culture is a supernatant of a peripheral blood mononuclear cell (PBMC) culture. A supernatant of cultivated PBMCs can be used in the treatment of inflammatory conditions (see e.g. WO 2010/070105 and WO 2010/079086). PBMCs as defined herein comprise or consist of T cells, B cells or/and NK cells.

According to a particularly preferred embodiment of the present invention the mammalian cells of the present invention are cultivated under stress inducing conditions. It is known in the art that mammalian cells are able to secrete sub-stances in the cultivation medium during cultivation. This effect may be even more enhanced if the mammalian cells are subjected during or before cultivation to stress inducing conditions. In particular stressed mammalian cells turned out to secrete substances which are particularly beneficial in the treatment of inflammatory conditions.

The term "under stress inducing conditions", as used herein, refers to cultivation conditions leading to stressed cells. Conditions causing stress to cells include among others heat, chemicals, radiation, hypoxia, osmotic pressure etc.

The stress inducing conditions include hypoxia, ozone, heat (e.g. more than 2° C., preferably more than 5° C., more preferably more than 10° C., higher than the optimal cultivation temperature of mammalian cells, i.e. 37° C.), radiation (e.g. UV radiation, ionizing radiation, gamma radiation), chemicals, osmotic pressure (i.e. osmotic conditions which are elevated at least in comparison to osmotic conditions regularly occur-ring in a body fluid, in particular in blood) or combinations thereof.

If radiation is used to stress the mammalian cells of the present invention the cells are preferably irradiated with at least 10 Gy, preferably at least 20 Gy, more preferably at least 40 Gy, whereby as source Cs-137 Caesium is preferably used.

According to a preferred embodiment of the present invention mammalian cells are cultivated for at least 4 h, preferably for at least 6 h, more preferably for at least 12 h, before isolating its supernatant.

According to the present invention the eukaryotic cells of step a) are preferably selected from the group consisting of adenocarcinomic human alveolar basal epithelial cells, preferably A549 cells, aneuploid immortal keratinocyte cells (HaCaT), human embryonic kidney cells (HEK cells), preferably HEK293 cells, and neuroblastoma cells, preferably SH-SY5Y cells. It turned out that in particular these eukaryotic cells can be used to determine the potency of supernatants of mammalian cell cultures to be used in the treatment of inflammatory conditions.

The eukaryotic cells of step a) are incubated (i.e. cultivated) in the cell culture medium for at least 2 hours, preferably at least 4 hours, more preferably at least 6 hours, more preferably at least 12 hours, more preferably at least 18 hours, more preferably at least 24 hours. A cultivation time of at least 2 hours is sufficient to allow the substances present in the culture medium comprising or consisting of a supernatant of a mammalian cell culture to increase the expression and optional secretion of phosphorylated HSP27 and/or to activate the promoters mentioned above.

The culture medium used in step a) comprises at least 20%, preferably at least 50%, more preferably at least 70%, more preferably at least 80%, more preferably at least 90%, more preferably at least 95%, or consists of a supernatant of a mammalian cell culture.

In a preferred embodiment of the present invention the culture medium of step a) is a Dulbecco's Modified Eagle Medium (DMEM), a Ham's F12 Medium (F12), a minimum essential medium or a combination of one or more of these media.

In another embodiment of the present invention the culture medium of step a) comprises 2 to 20%, preferably 5 to 15%, fetal bovine serum (FBS) and/or L-alanyl-L-glutamine.

In order to determine the promoter activity of the above mentioned promoters in the eukaryotic cells the cells are preferably genetically modified to comprise at least one expression cassette comprising a promoter selected from the group consisting of an AP-1 promoter, NF-κB promoter, Sox2 promoter, STAT3 promoter, EGR-1 promoter and SRE promoter operably linked to at least one nucleic acid molecule encoding for a reporter protein.

An "expression cassette", as defined herein, refers to a nucleic acid fragment which contains a gene (i.e. a nucleic acid molecule encoding a protein or polypeptide) operably linked to regulatory sequences necessary for gene expression.

"Operably linked" refers to the linking of nucleotide regions encoding specific genetic information such that the nucleotide regions are contiguous, the functionality of the region is preserved and will perform relative to the other regions as part of a functional unit.

The expression cassette introduced into the eukaryotic cells may be provided as part of a vector. A "vector" is considered to be a vehicle by means of which nucleic acid fragments can be introduced into host organisms like eukaryotic cells. An "expression vector" is a vehicle by means of which nucleic acid fragments and in particular expression cassettes that contain sufficient genetic information can be introduced into eukaryotic cells and can, therefore, be expressed by these cells.

The reporter protein encoded by the expression cassette may be a polypeptide or protein which can be bound by an antibody or antigen binding fragment thereof, an enzyme or a fluorescent protein or polypeptide. The reporter protein is preferably selected from the group consisting of a luciferase, preferably a firefly luciferase, a fluorescent protein, preferably a green fluorescent protein.

"Luciferases" are oxidative enzymes that are able to produce bioluminescence in the presence of luciferin, oxygen and ATP. "Fluorescent proteins" are proteins that have fluorescent properties.

The amount of proteins (e.g. phosphorylated HSP27, re-porter proteins) released by the eukaryotic cells into the culture medium is determined by an immunological method, preferably by enzyme-linked immunosorbent assay (ELISA), by a photometrical method or by a fluorescent method.

Adenocarcinomic human alveolar basal epithelial cells, preferably A549 cells, HaCaT or HEK cells, preferably HEK293 cells, turned out to be in particular suitable for determining the amount of phosphorylated HSP27.

If the promoter activity of the at least one promoter is preferably at least 80%, preferably at least 100%, more preferably at least 150%, more preferably at least 200%, higher compared to the promoter activity measured when the eukaryotic cells are cultivated in a culture medium lacking said supernatant the supernatant of a mammalian cell culture can be used in the treatment of an inflammatory condition.

The eukaryotic cells of step a) are preferably adenocarcinomic human alveolar basal epithelial cells, preferably A549 cells, HaCaT cells or HEK cells, preferably HEK293 cells, when the amount of phosphorylated HSP27 released into the culture medium is measured.

The eukaryotic cells of step a) are preferably neuroblastoma cells, preferably SH-SY5Y cells, or HaCaT cells comprising at least one expression cassette comprising an AP-1 promoter operably linked to at least one nucleic acid molecule encoding for a reporter protein.

The eukaryotic cells of step a) are preferably adenocarcinomic human alveolar basal epithelial cells, preferably A549 cells, comprising at least one expression cassette comprising an NF-κB or Sox2 promoter operably linked to at least one nucleic acid molecule encoding for a reporter protein.

The eukaryotic cells of step a) are preferably HEK cells, preferably HEK293 cells, comprising at least one expression cassette comprising an EGR-1, SRE, AP-1 or STAT3 promoter operably linked to at least one nucleic acid molecule encoding for a reporter protein.

The present invention is further illustrated by the following embodiments and examples, however, without being restricted thereto.

Embodiments of the Invention

1. A method for determining the potency of a supernatant of a mammalian cell culture to be used in the treatment of an inflammatory condition comprising the steps of
  a) incubating eukaryotic cells in a culture medium comprising or consisting of said supernatant,
  b) measuring a promoter activity of at least one promoter selected from the group consisting of activator protein (AP-1) promoter, nuclear factor kappa-light-chain-enhancer of activated B cells (NF-κB) promoter, sex determining region Y-box 2 (Sox2) promoter, signal transducer and activator of transcription 3 (STAT3) promoter, early growth response protein 1 (EGR-1) promoter and serum response element (SRE) promoter and/or measuring the amount of phosphorylated heat shock protein 27 (HSP27) released by the eukaryotic cells into the culture medium of step a),
  wherein the supernatant of the mammalian cell culture has the potential to be used in the treatment of an inflammatory condition, if the promoter activity of the at least one promoter is at least 50% higher compared to the promoter activity measured when the eukaryotic cells are cultivated in a culture medium lacking said supernatant and/or if the amount of phosphorylated HSP27 released into the culture medium of step a) is at least 20% higher compared to the amount of phosphorylated HSP27 released into the culture medium when the eukaryotic cells are cultivated in a culture medium lacking said supernatant.

2. A method for determining the potency of a supernatant of a mammalian cell culture to be used in the treatment of an inflammatory condition comprising the steps of
   a) incubating eukaryotic cells in a culture medium comprising or consisting of said supernatant,
   b) measuring a promoter activity of at least one promoter selected from the group consisting of activator protein 1 (AP-1) promoter, nuclear factor kappa-light-chain-enhancer of activated B cells (NF-κB) promoter, sex determining region Y-box 2 (Sox2) promoter, signal transducer and activator of transcription 3 (STAT3) promoter, early growth response protein 1 (EGR-1) promoter and serum response element (SRE) promoter and/or measuring the amount of phosphorylated heat shock protein 27 (HSP27) released by the eukaryotic cells into the culture medium of step a),
   wherein the supernatant of the mammalian cell culture has the potential to be used in the treatment of an inflammatory condition, if the promoter activity of the at least one promoter is up to 25% higher or lower compared to the promoter activity measured when the eukaryotic cells are cultivated in a culture medium comprising a reference supernatant of mammalian cells, which can be used in the treatment of an inflammatory condition and/or if the amount of phosphorylated HSP27 released into the culture medium of step a) is up to 25% higher or lower compared to the amount of phosphorylated HSP27 released into the culture medium of step a) comprising a reference supernatant of mammalian cells, which can be used in the treatment of an inflammatory condition.

3. Method according to embodiment 1 or 2, wherein the supernatant of a mammalian cell culture is a supernatant of a peripheral blood mononuclear cell (PBMC) culture.

4. Method according to any one of embodiments 1 to 3 2, wherein the mammalian cell culture comprises T cells, B cells and/or NK cells.

5. Method according to any one of embodiments 1 to 4, wherein the mammalian cells in the mammalian cell culture are cultivated in a cell culture medium selected from the group consisting of a cell growth medium, preferably CellGro medium, more preferably Cellgro GMP DC medium, RPMI, DMEM, X-vivo and Ultraculture.

6. Method according to any one of embodiments 1 to 5, wherein the mammalian cells are subjected to one or more stress inducing conditions before or during cultivation.

7. Method according to embodiment 6, wherein the stress inducing condition is selected from the group consisting of radiation, in particular ionizing radiation or UV radiation, hypoxia, ozone, heat, osmotic pressure and pH shift.

8. Method according to embodiment 7, wherein the mammalian cells are subjected to an ionizing radiation at a dose of at least 10 Gy, preferably at least 20 Gy, more preferably at least 40 Gy.

9. Method according to any one of embodiments 1 to 8, wherein the mammalian cells are cultivated for at least 4 h, preferably for at least 6 h, more preferably for at least 12 h, before isolating its supernatant.

10. Method according to any one of embodiments 1 to 9, wherein the inflammatory condition is a condition associated with ischemia, preferably a skin condition or an internal inflammatory condition.

11. Method according to any one of embodiments 1 to 10, wherein the eukaryotic cells of step a) are selected from the group consisting of adenocarcinomic human alveolar basal epithelial cells, preferably A549 cells, aneuploid immortal keratinocyte cells (HaCaT), human embryonic kidney cells (HEK cells), preferably HEK293 cells, and neuroblastoma cells, preferably SH-SY5Y cells.

12. Method according to any one of embodiments 1 to 11, wherein the eukaryotic cells of step a) are incubated in the cell culture medium for at least 2 hours, preferably at least 4 hours, more preferably at least 6 hours, more preferably at least 12 hours, more preferably at least 18 hours, more preferably at least 24 hours.

13. Method according to any one of embodiments 1 to 12, wherein the culture medium comprises at least 20%, preferably at least 50%, more preferably at least 70%, more preferably at least 80%, more preferably at least 90%, more preferably at least 95%, of said supernatant.

14. Method according to any one of embodiments 1 to 13, wherein the culture medium of step a) is a Dulbecco's Modified Eagle Medium (DMEM), a Ham's F12 Medium (F12), a minimum essential medium or a combination of one or more of these media.

15. Method according to any one of embodiments 1 to 14, wherein the culture medium of step a) comprises 2 to 20%, preferably 5 to 15%, fetal bovine serum (FBS) and/or L-alanyl-L-glutamine 16. Method according to any one of embodiments 1 to 15, wherein the eukaryotic cells comprise at least one expression cassette comprising a promoter selected from the group consisting of an AP-1 promoter, NF-κB promoter, Sox2 promoter, STAT3 promoter, EGR-1 promoter and SRE promoter operably linked to at least one nucleic acid molecule encoding for a reporter protein.

17. Method according to embodiment 16, wherein the reporter protein is selected from the group consisting of a luciferase, preferably a firefly luciferase, and a fluorescent protein, preferably a green fluorescent protein.

18. Method according to any one of embodiments 1 to 17, wherein the amount of the protein released by the cells into the culture medium is determined by an immunological method, preferably by enzyme-linked immunosorbent assay (ELISA), by a photometrical method or by a fluorescent method.

19. Method according to any one of embodiments 1 to 18, wherein the eukaryotic cells of step a) are adenocarcinomic human alveolar basal epithelial cells, preferably A549 cells, HaCaT or HEK cells, preferably HEK293 cells, and the amount of phosphorylated HSP27 is determined.

20. Method according to any one of embodiments 1 to 19, wherein the promoter activity of the at least one promoter is at least 80%, preferably at least 100%, more preferably at least 150%, more preferably at least 200%, higher compared to the promoter activity measured when the eukaryotic cells are cultivated in a culture medium lacking said supernatant.

21. Method according to any one of embodiments 1 to 20, wherein the eukaryotic cells of step a) are adenocarcinomic human alveolar basal epithelial cells, preferably A549 cells, HaCaT cells or HEK cells, preferably HEK293 cells, when the amount of phosphorylated HSP27 released into the culture medium is measured.

22. Method according to any one of embodiments 1 to 21, wherein the eukaryotic cells of step a) are neuroblastoma cells, preferably SH-SY5Y cells, or HaCaT cells comprising at least one expression cassette comprising an AP-1 promoter operably linked to at least one nucleic acid molecule encoding for a reporter protein.

23. Method according to any one of embodiments 1 to 22, wherein the eukaryotic cells of step a) are adenocarcinomic human alveolar basal epithelial cells, preferably A549 cells, comprising at least one expression cassette comprising an NF-κB or Sox2 promoter operably linked to at least one nucleic acid molecule encoding for a reporter protein.

24. Method according to any one of embodiments 1 to 23, wherein the eukaryotic cells of step a) are HEK cells, preferably HEK293 cells, comprising at least one expression cassette comprising an EGR-1, SRE, AP-1 or STAT3 promoter operably linked to at least one nucleic acid molecule encoding for a reporter protein.

EXAMPLES

Example 1: Production of Aposec

"Aposec" is a supernatant of a mammalian cell culture which can be obtained by cultivating mammalian cells, in particular PBMCs, using stress inducing conditions like irradiation, hypoxia etc. before or during cultivation of said cells. The methods are described above, in WO 2010/079086 and in WO 2010/070105 and in particular in Lichtenauer M et al (Basic Res Cardiol. 2011; 106: 1283-1297).

In detail, human PBMC were obtained from young healthy volunteers. Cells were separated by Ficoll-Paque (GE Healthcare Bio-Sciences AB, Sweden) density gradient centrifugation as described in Ankersmit H J et al. (Eur J Clin Invest. 2009; 39:445-456). Apoptosis of PBMC was induced by Caesium-137 irradiation with 60 Gray (Gy). Induction of apoptosis was measured by Annexin-V/propidium iodine (FITC/PI) co-staining (Becton-Dickinson, Franklin Lakes, N.J., USA) on a flow cytometer. Irradiated and non-irradiated cells were resuspended in serum-free UltraCulture Medium (Lonza, Switzerland) or Cellgro GMP DC medium (CellGenix, Freiburg, Germany), and cultured for 24 h in various cell densities ($1 \times 10^6$, $2.5 \times 10^6$ and $25 \times 10^6$ cells/ml, n=5). After 24 h supernatants were collected and served as experimental entities for the following experiments (see below) or were lyophilized as follows: supernatants were dialyzed against ammonium acetate (at a concentration of 50 mM) for 24 h at 4° C. The obtained liquid was sterile filtered (Whatman Filter 0.2 μm FP30/o,2 Ca—S, Germany), frozen and lyophilized overnight (Lyophilizator Christ alpha 1-4, Martin Christ Gefriertrock-nungsanlagen GmbH, Germany).

Example 2: Proliferation Assay

HUVEC (human umbilical vein endothelial cells), NHDF (normal human dermal fibroblasts) and A549 (human epithelial-like carcinoma cells) cells were seeded at three different cell densities into 96-well plates and were treated with Aposec (2.5 U/mL), bFGF (20 ng/mL) and TNFa (4 ng/mL). In addition to the cell numbers and treatments, the cells were cultivated with different percentages of growth medium. After an overnight incubation in the $CO_2$-incubator, the cell number was determined using CellTiter-Glo Luminescent Cell Viability As-say (CellTiterGlo), which is a homogeneous method of determining the number of viable cells in culture based on quantitation of the ATP present (it is an indicator of metabolically active cells) (see Technical Bulletin, CellTiter-Glo Luminescent Cell Viability Assay, Promega, TB288, Revised 3/15).

Figure 1B:
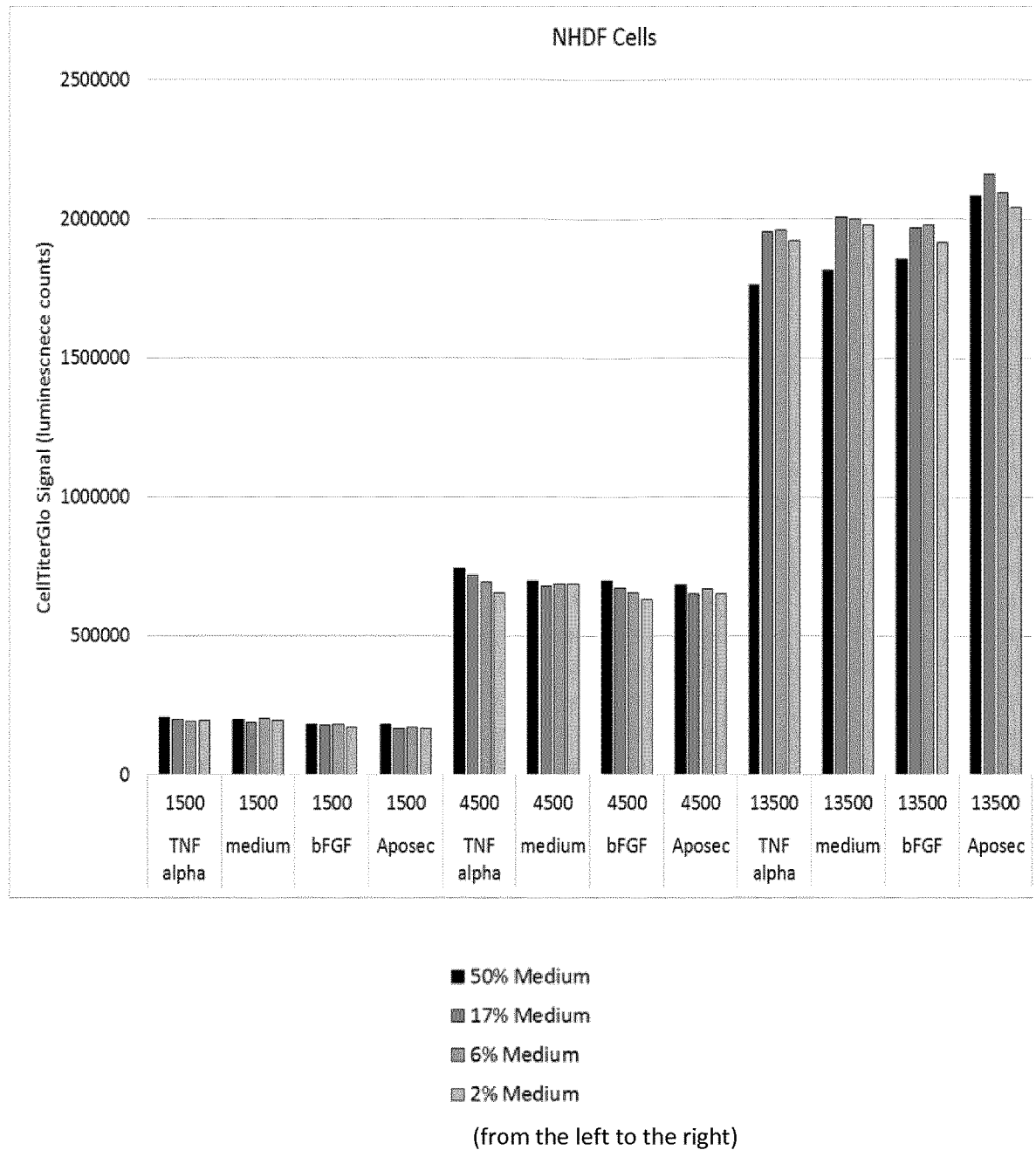
Figure 1C:
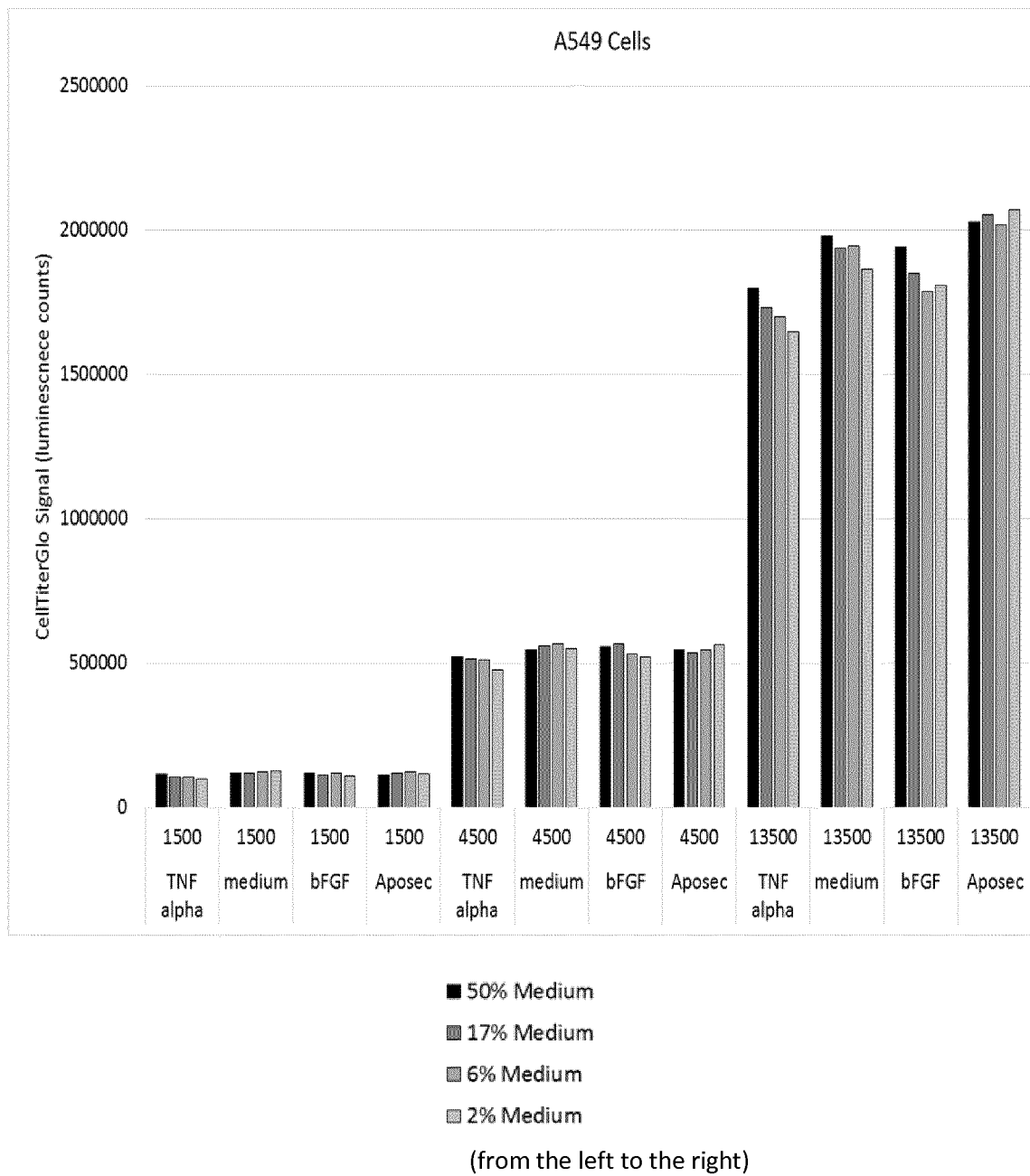

A clear cell density dependent cell number was observed upon the overnight incubation. No sign for a proliferation induction by Aposec could be observed (see FIG. 1).

Example 3: Determination of Phosphorylated HSP27

In this example it was investigated whether Aposec is able to induce the phosphorylation of Hsp27 in vitro.

Generally speaking different antibodies specific for human Hsp27, human phospho-Ser15-Hsp27 and human phsopho-Ser82-Hsp27 were evaluated in a cellular ELISA with different human cell lines (A549, HaCat and HEK293 cells). The cellular ELISA was based on the following principle: cells were grown in 96-well plates and at the end of the treatment/stimulation period, the cells were fixed and permeabilized. The phosphory-lation can be quantified by sequential addition of an antibody that detects phosphorylated Hsp27 (e.g. phospho-Hsp27(Ser82)), followed by a peroxidase-conjugated anti-rabbit IgG antibody (detection antibody), and a chemiluminescent peroxi-dase substrate.

The table below lists the evaluated human Hsp27 specific antibodies:

| Type | Species | mono/polyclonal | Source | Catalog no. |
|---|---|---|---|---|
| Hsp27 total | mouse | monoclonal G31 | Cell Signaling Technology | 2402 |
| Hsp27 total | mouse | monoclonal F-4 | Santa Cruz | sc-13132 |
| Hsp27 Ser82 | rabbit | monoclonal D1H2F6 | Cell Signaling Technology | 9709 |
| Hsp27 Ser15 | rabbit | polyclonal | ThermoFisher/ Invitrogen | PA1-018 |

3.1 Cellular Hsp27 ELISA Assay 1

A549, HEK293 and HaCat cells were treated for 2 hours with a combination of sulforaphane (20 μM) and thapsigargin (1 μM) to induce Hsp27 phosphorylation and with the MAPK inhibitor SB203580 (20 μM). The fixed, permeabilized and blocked cells, were incubated overnight at 4° C. with different concentrations of the antibodies.

Figure 2:
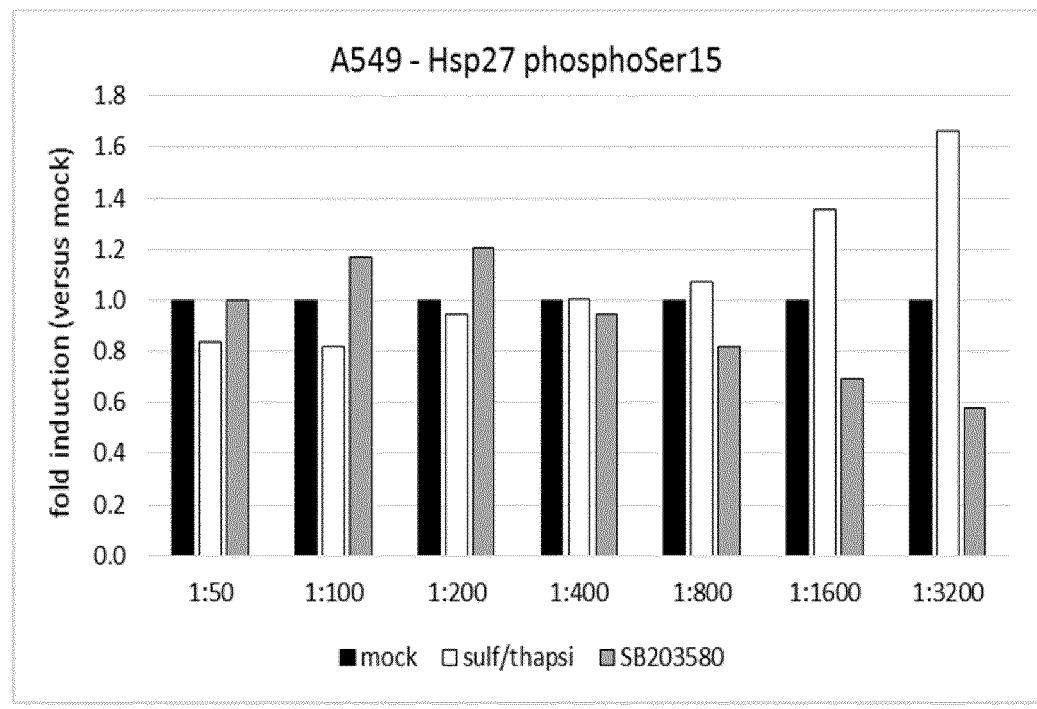
FIG. 2 shows the results of Cellular Hsp27 ELISA assay 1 (see example 3)
Figure 2:
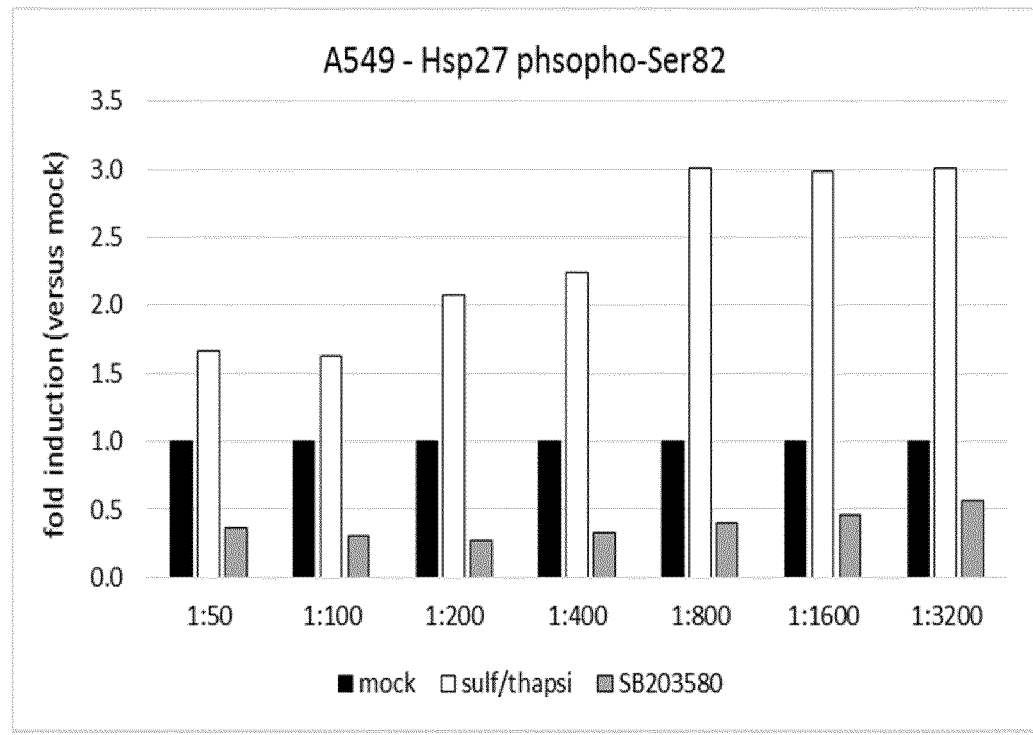
Figure 2:
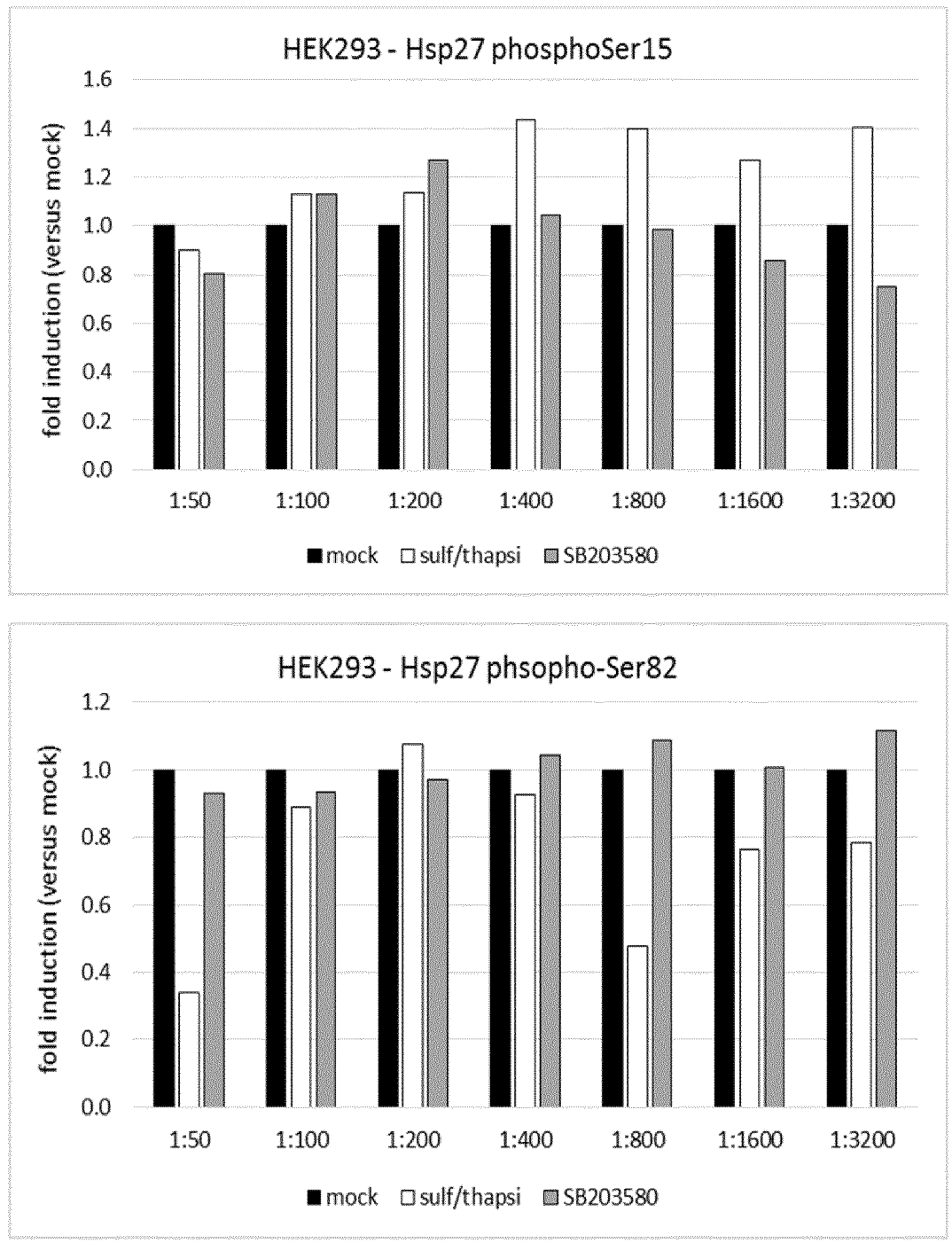
Figure 2:
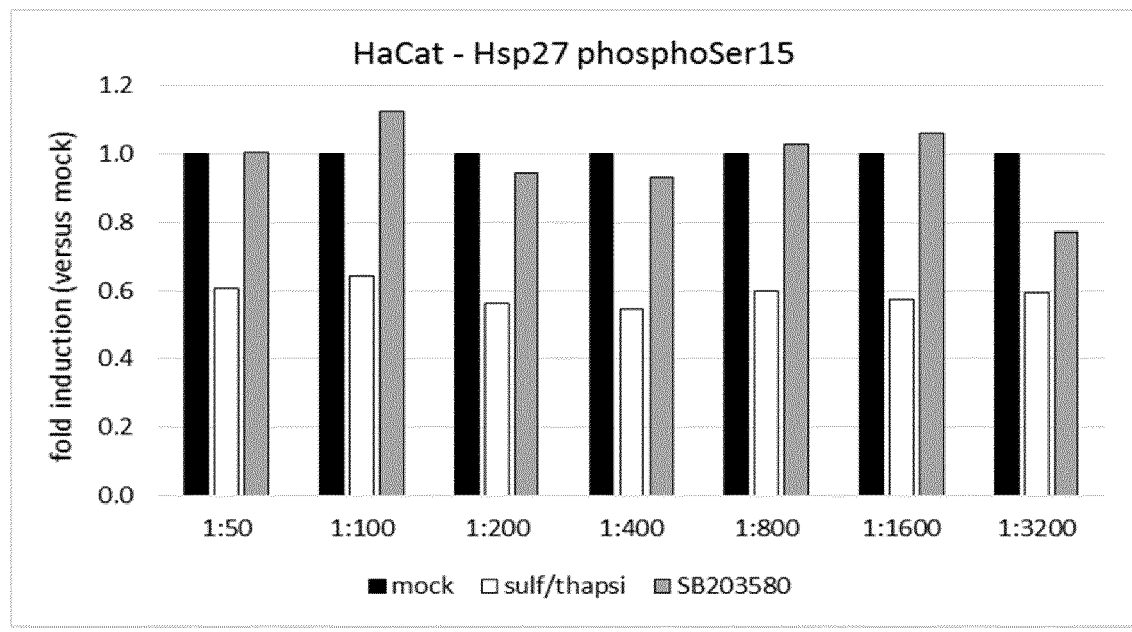
Figure 2:
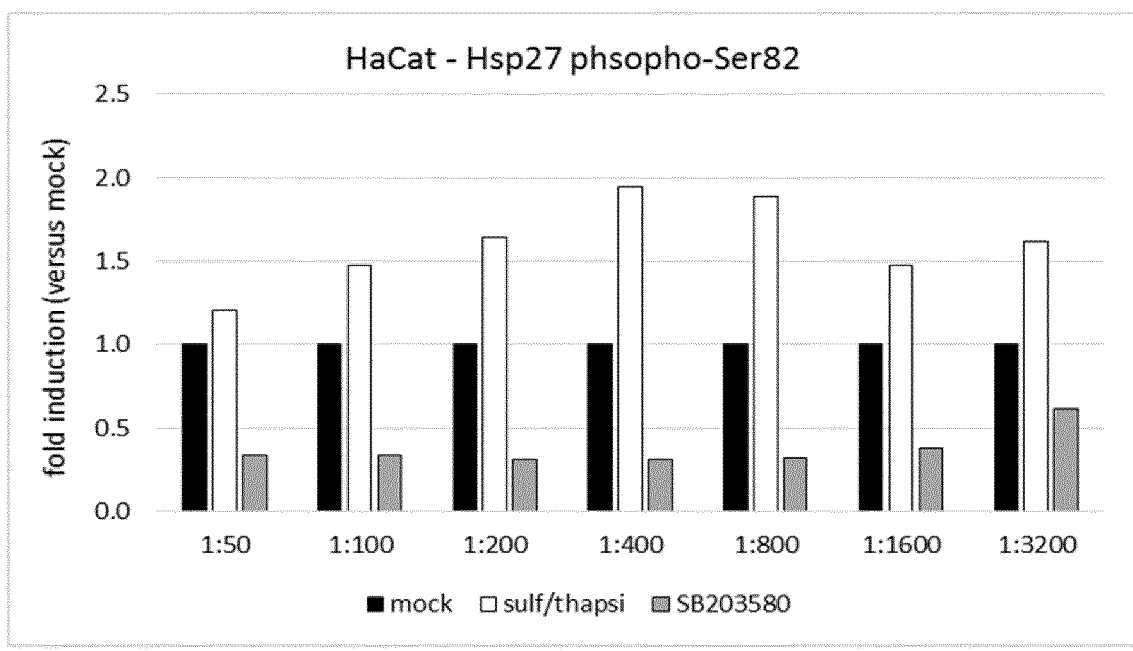

The treatment and antibody-concentration dependent signals are expressed relative to the mock treated cells that were incubated with the same antibody concentration (see FIG. 2).

The phospoSer82-Hsp27 antibody shows the expected pattern in A549 and HaCat cells. The co-treatment with sulforaphane/thapsigargin leads to the expected increase in the phospoSer82-Hsp27 signal, while the MAPK inhibitor reduces the signal: MAPK is upstream of Hsp27. In A549 cells, higher antibody dilutions (less antibody) result in a higher relative induction, most likely because of a reduced unspecific signal.

3.2 Cellular Hsp27 ELISA Assay 2

A549, HEK293, HaCat and SHSY5Y cells were treated for 2 hours with different concentrations of Aposec, sulforaphane and thapsigargin, in the absence or presence of the MAPK inhibitor SB203580. The fixed, permeabilized and blocked cells, were incubated overnight at 4° C. with two different concentrations of the phospoSer15-Hsp27 (1:3200 and 1:6400) and the phospoSer82-Hsp27 (1:800 and 1:1600) antibody.

Figure 3:
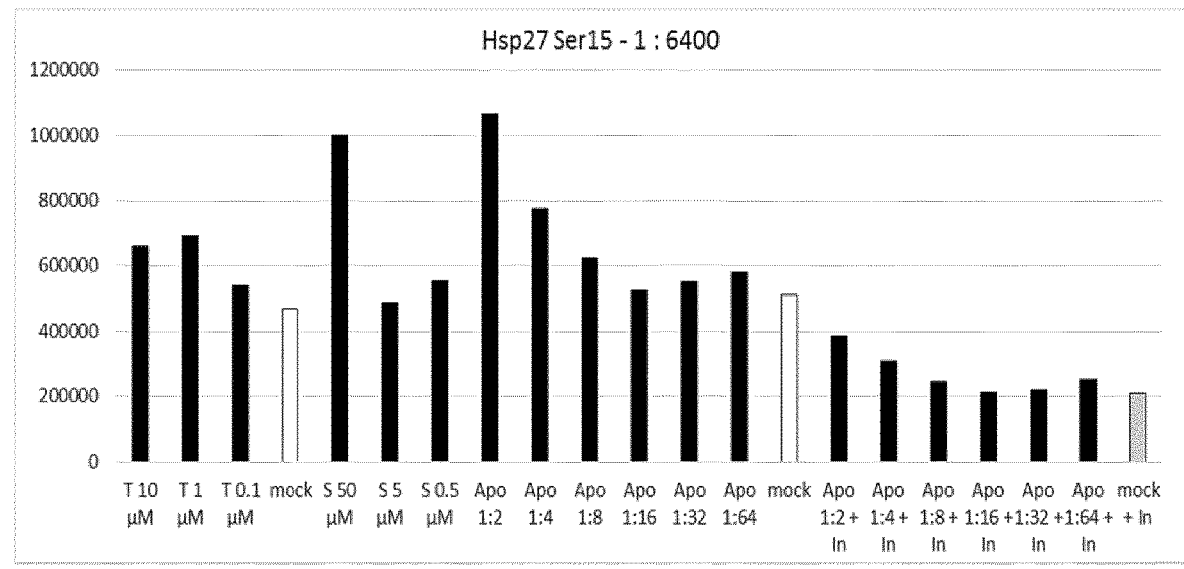
FIG. 3 shows the results of Cellular Hsp27 ELISA assay 2 (see example 3).
Figure 3:
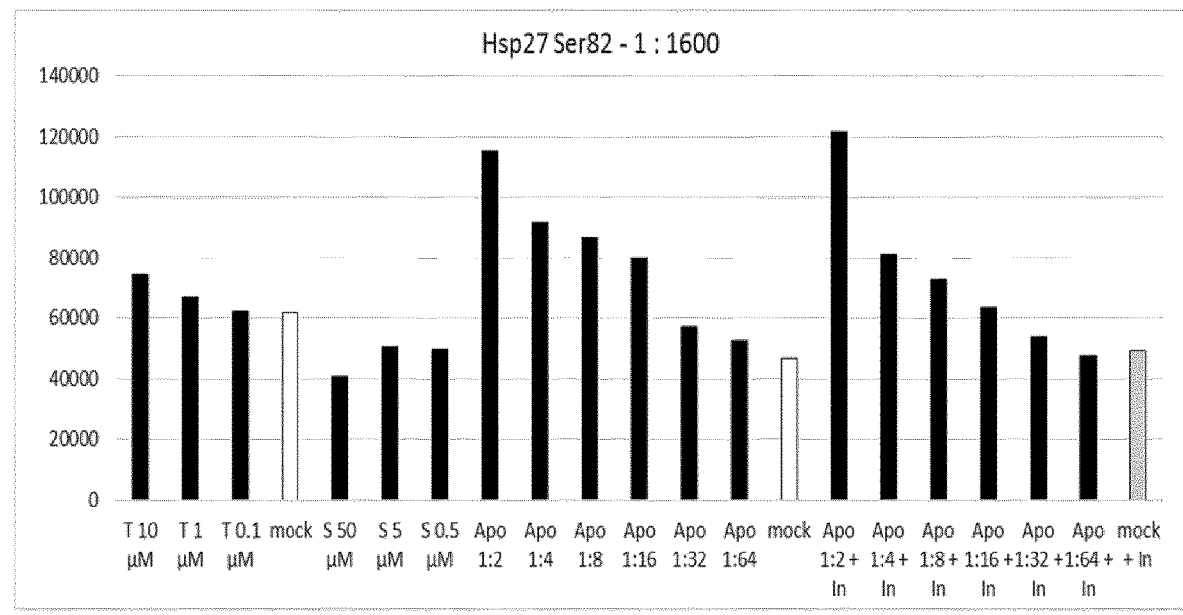
Figure 3:
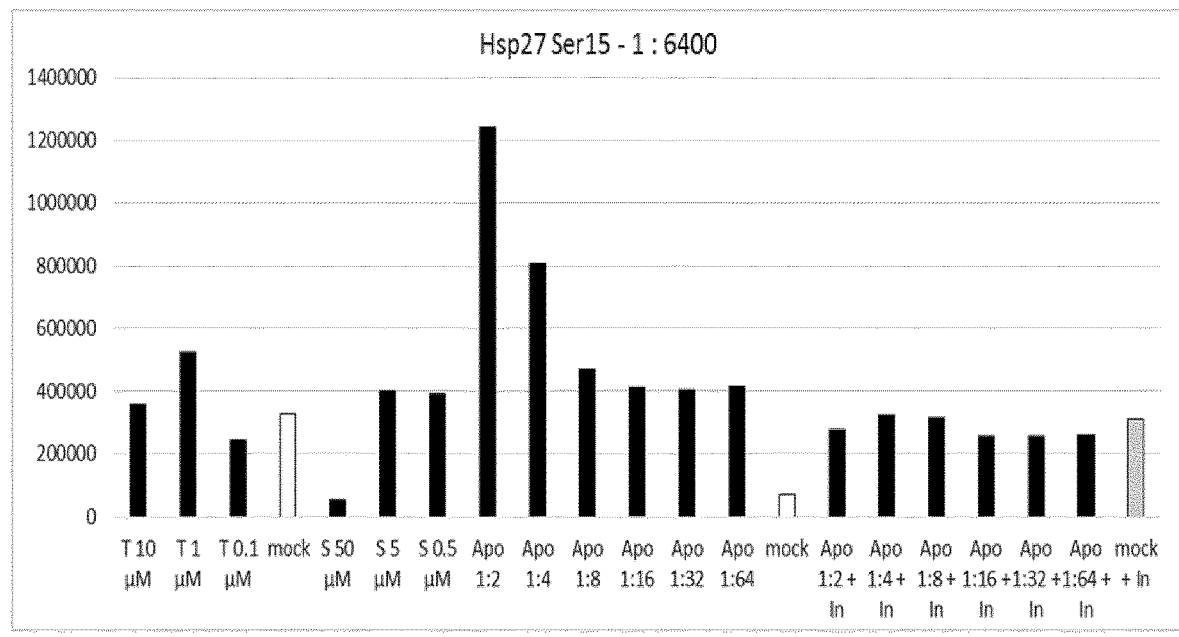
Figure 3:
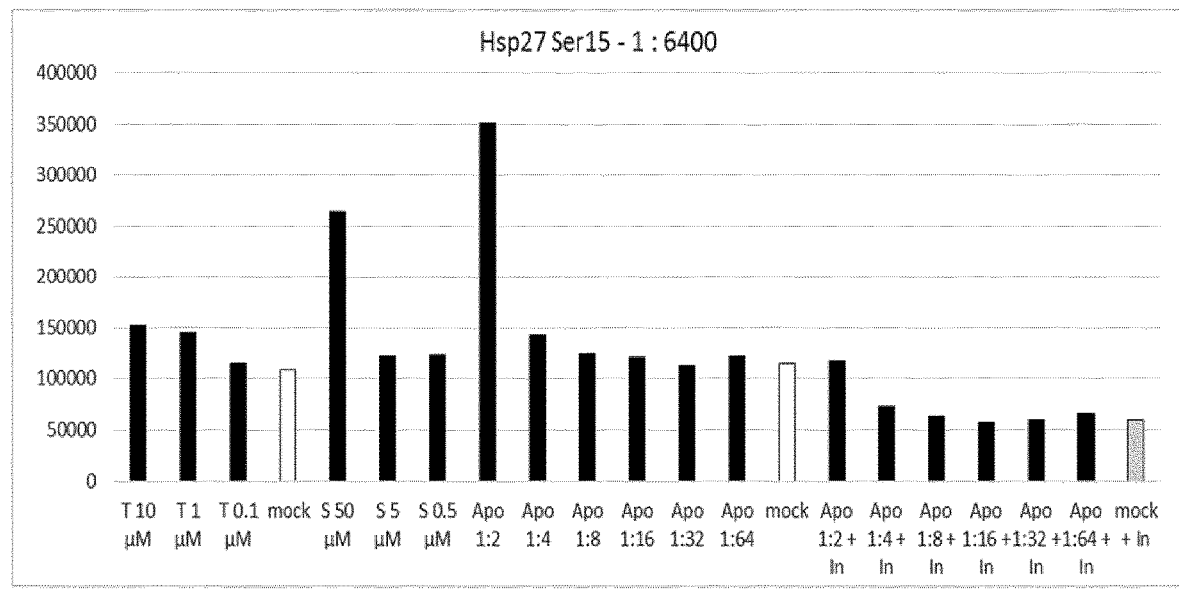
Figure 3:
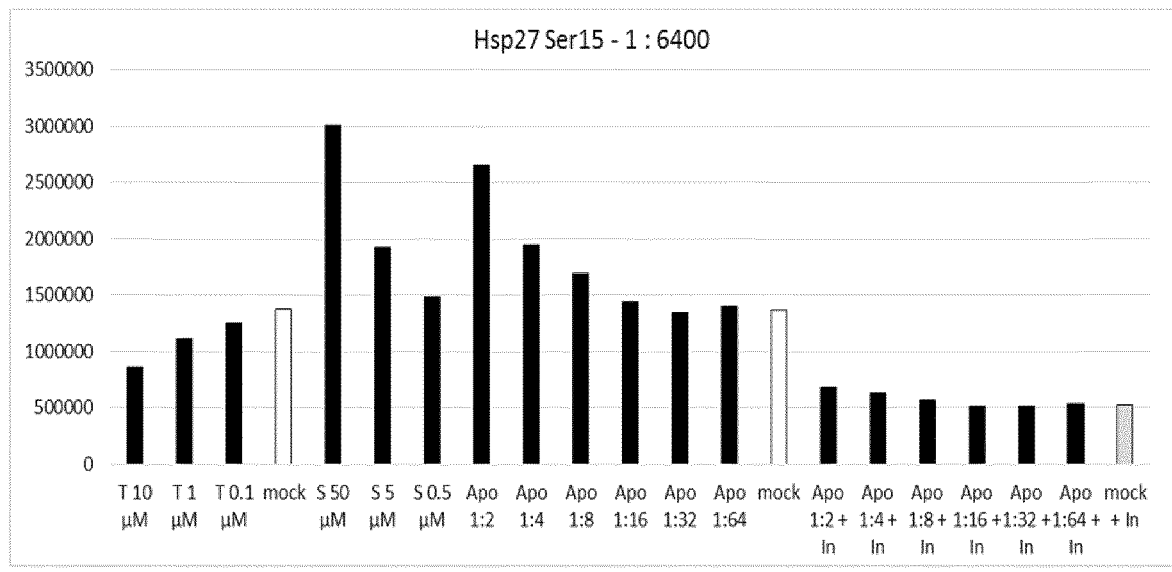

The comparison of the two antibody concentrations tested has revealed for both antibodies, that the higher dilution results in a better signal-to-noise ratio. In the A549 cells, a dose-dependent induction of phospoSer15-Hsp27 and phospoS-er82-Hsp27 was observed. The induction of phospoSer15-Hsp27, but not the induction of phospoSer82-Hsp27, was prevented by the MAPK inhibitor SB203580 in the A549 cells. In the other three tested cell lines (HEK293, HaCat and SH-SY5Y), phospoS-er15-Hsp27 was induced by Aposec (see FIG. 3).

3.3 Cellular Hsp27 ELISA Assay 3

In this part of example 3 it is investigated whether the so far observed phospoSer15-Hsp27 and phospoSer82-Hsp27 induction upon Aposec treatment is specific for Aposec.

A549 cells were treated for 1 hour with different concentrations of Aposec and CellGro. The lyophilisates used, had been reconstituted either with 0.9% NaCl or with $H_2O$, to evaluate the effect of the NaCl concentration in Aposec and CellGro. The fixed, permeabilized and blocked cells, were incubated overnight at 4° C. with one concentration of the phospoSer82-Hsp27 antibody. Beside the comparison of Aposec vs. CellGro and 0.9% NaCl or $H_2O$, beside, a 15, 30 or 60 minutes treatment was evaluated for Aposec and CellGro (reconstituted in $H_2O$).

Figure 4:
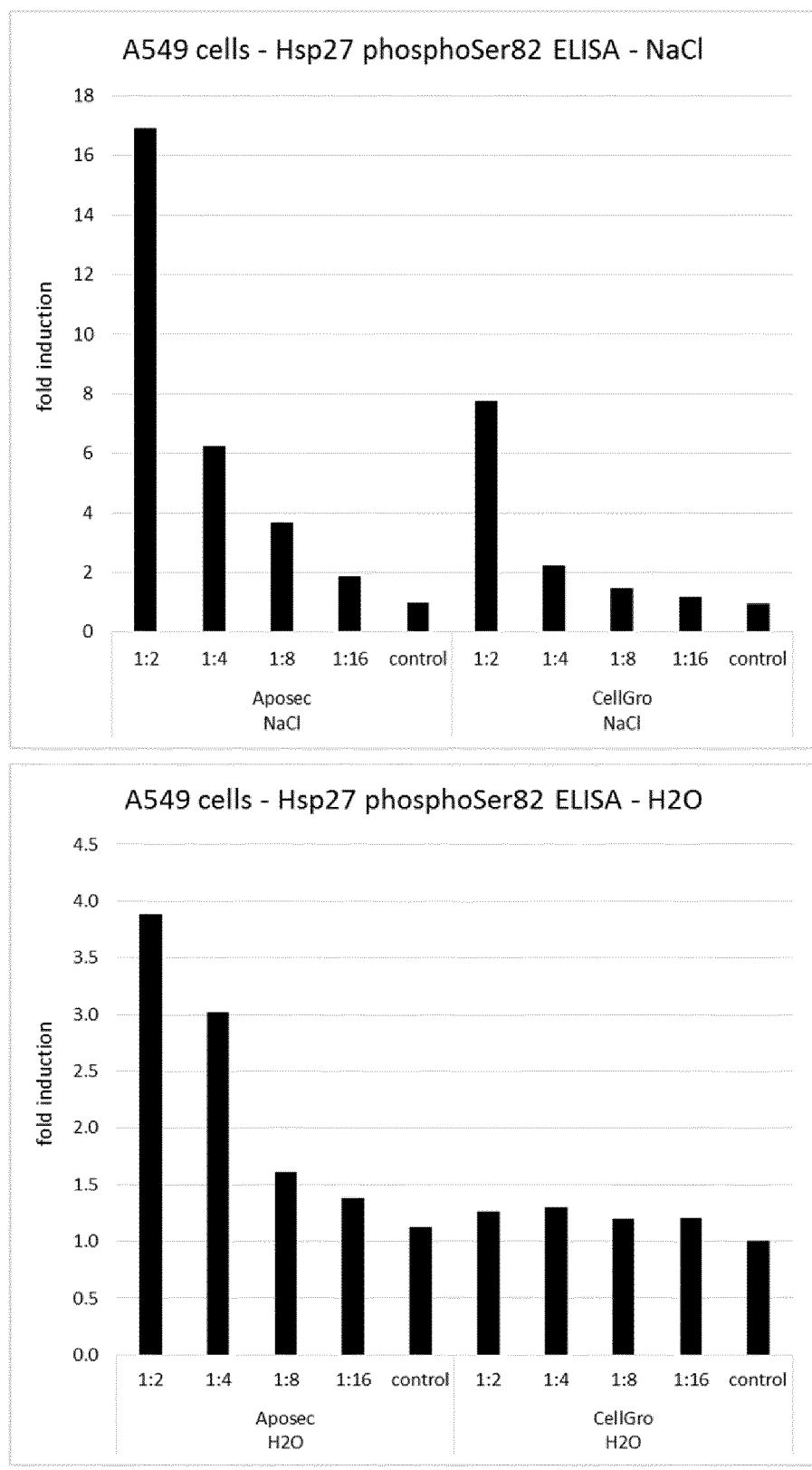
FIG. 4 shows the results of Cellular Hsp27 ELISA assay 3 (see example 3).
Figure 4:
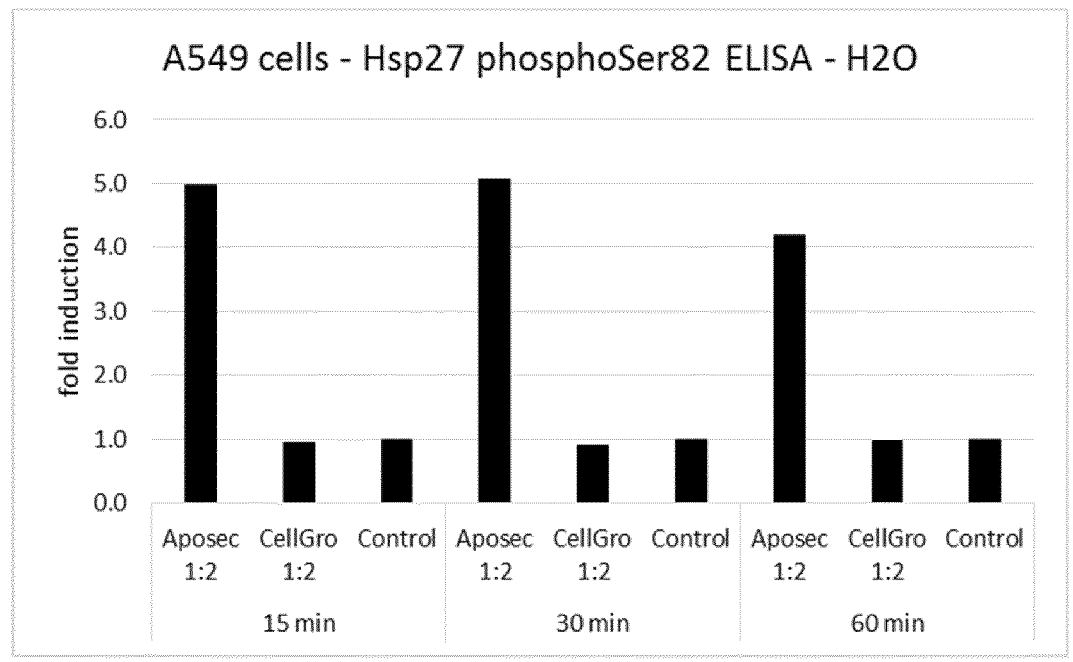

The comparison of the phospoSer82-Hsp27 induction by Aposec and CellGro, either reconstituted in $H_2O$ or 0.9% NaCl, shows, that CellGro reconstituted with $H_2O$ does not induce phospoSer82-Hsp27 and that CellGro reconstituted with 0.9% NaCl does induce much less phospoSer82-Hsp27 compared to Aposec reconstituted with 0.9% NaCl. The kinetic shows, that 15 and 30 minutes stimulation with Aposec results in a comparable induction (5-fold), while the induction is about 4-fold upon 1 hour stimulation (see FIG. 4).

3.4 Cellular Hsp27 ELISA Assay—Assay Range

In this part of example 3 it was investigated which as-say range for Aposec can be quantified with the phospoSer82-Hsp27 assay.

25%, 50% and 200% Aposec and 100% CellGro samples were used to treat A549 cells and the data was analyzed in PLA using a 4PL full curve model.

Figure 5:
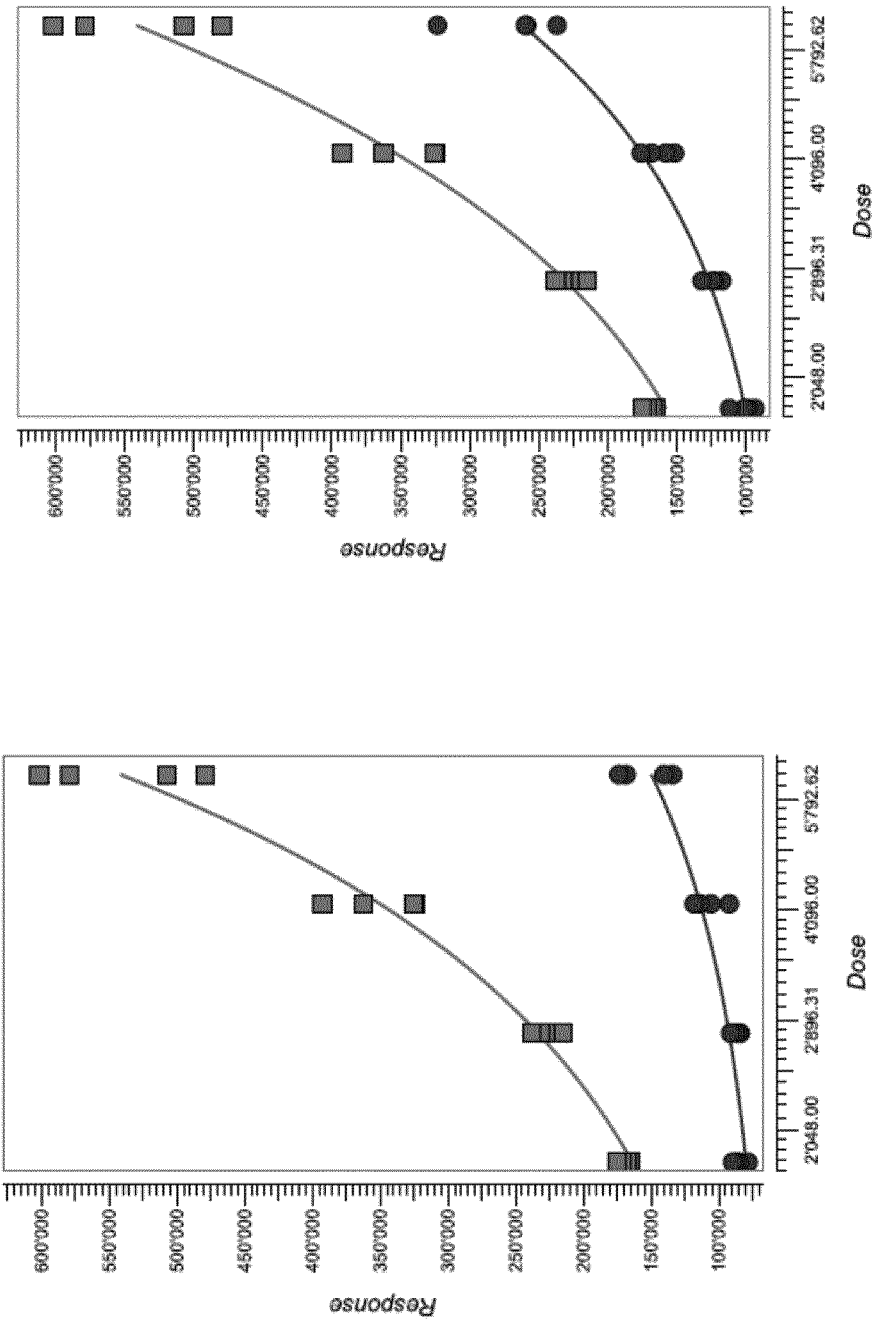
FIG. 5 shows the relative potency of various concentrations of Aposec in relation to 100% CellGro medium using an phosphorylated HSP27 assay as described in example 3.
Figure 5:
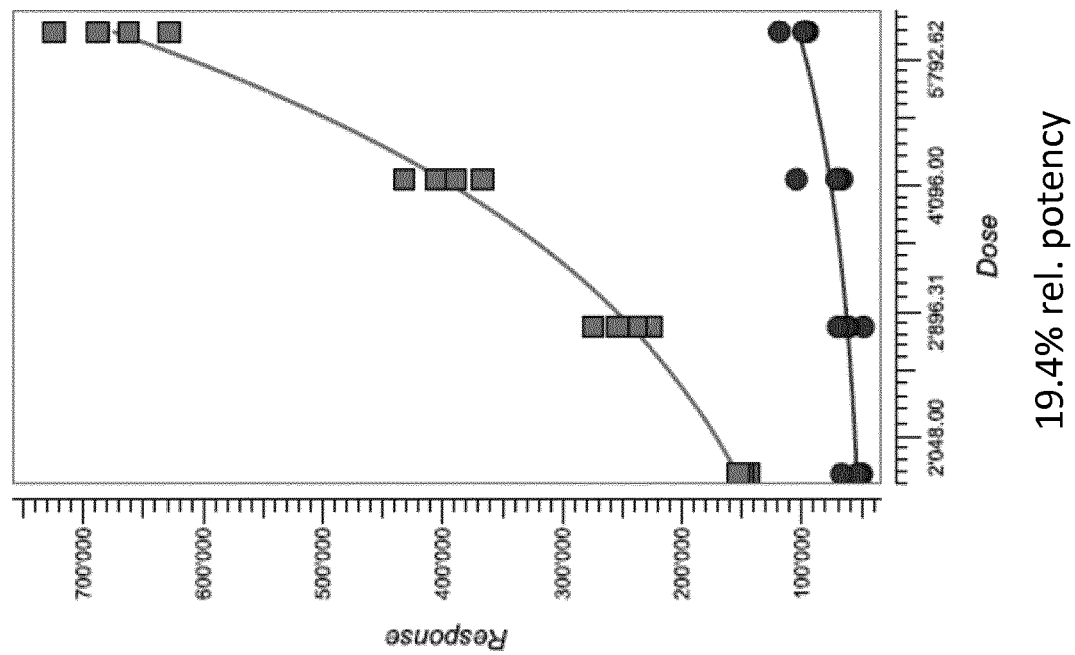
Figure 5:
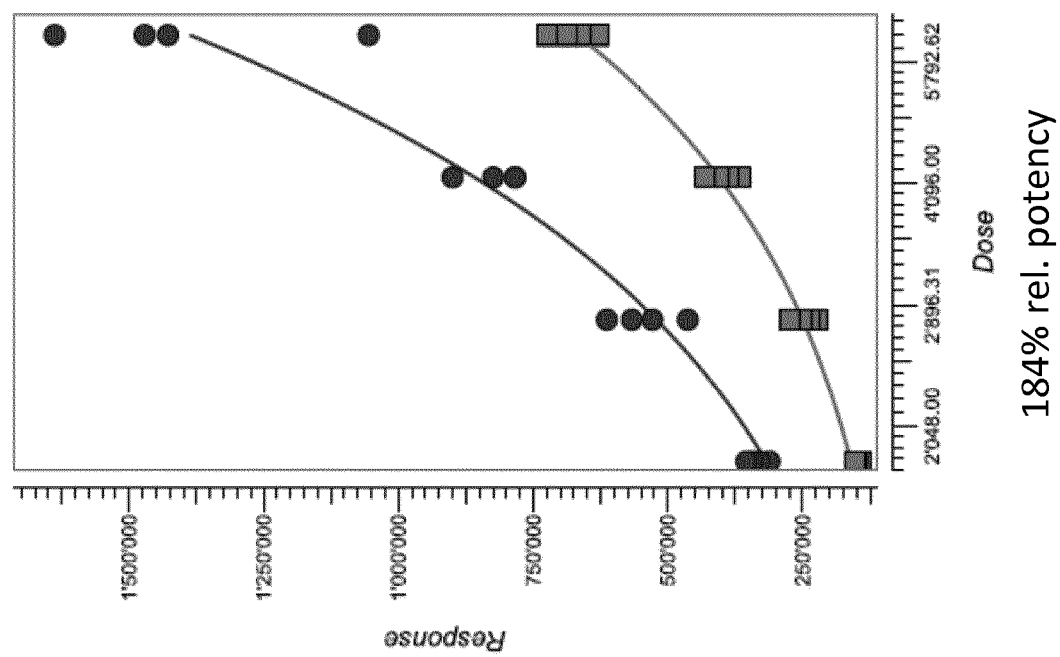

The PLA fitted curves are shown FIG. 5 and the resulting relative potencies are written below the graphs.

The assay allows quantifying Aposec relative potencies from 25% to 200%. The relative potency of CellGro is in the range of 20%. This CellGro activity reflects an unspecific effect caused by the reconstitution of the lyophilisate with 0.9% NaCl.

Example 4: AP-1 Reporter Gene Assay

In this example the question whether Aposec does induce the AP-1 promoter in vitro is addressed.

AP-1 reporter gene assay (RGA) cells (Brasier A R, et al. Methods Enzymol. 1992; 216:386-97) were generated using lentiviral particles (QIAGEN Order No. CLS-011L) expressing the AP-1 (activator protein 1) transcription factor-responsive reporter gene (firefly luciferase) (QIAGEN, Cignal Lenti Reporter Handbook For lentiviral-based cell signaling activity assays, Document No. 1073762; August 2012). The AP-1 RGA cells are stimulated with different amounts of Aposec. If Aposec stimulates the AP-1 promoter, firefly luciferase is expressed. At the end of the stimulation period with APOSEC, the cells are lysed, and luciferase activity is determined using a glow-type luciferase reagent.

4.1 AP-1 RGA Assay 1

In this part of example 4 it is investigated whether Aposec is able to stimulated the AP-1 promoter in different cell lines.

Three different cell lines that are stable transformed with an AP-1 promoter reporter construct, were stimulated with different dilutions of Aposec for 5 or 24 hours.

Figure 6:
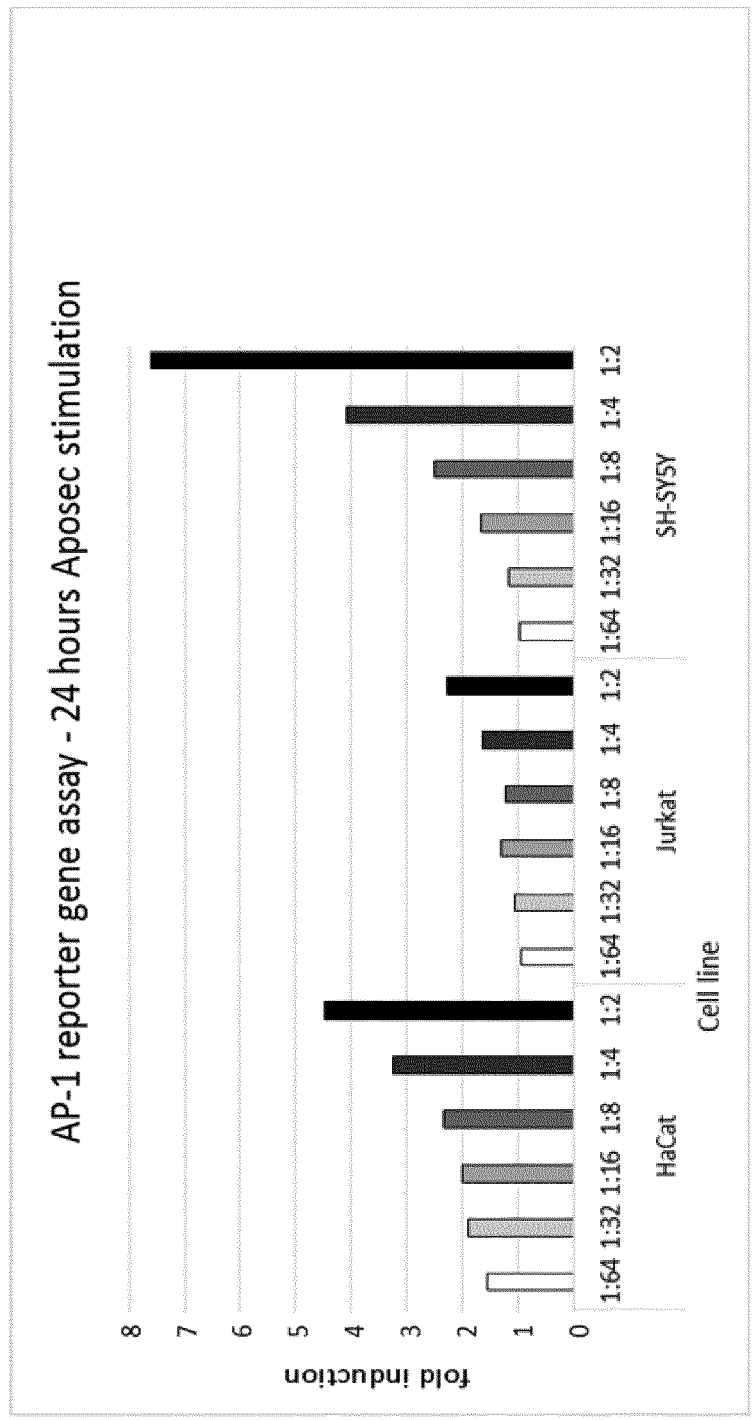
FIG. 6 shows the AP-1 reporter signal in eukaryotic cells stimulated with Aposec after 5 and 24 hours.
Figure 6:
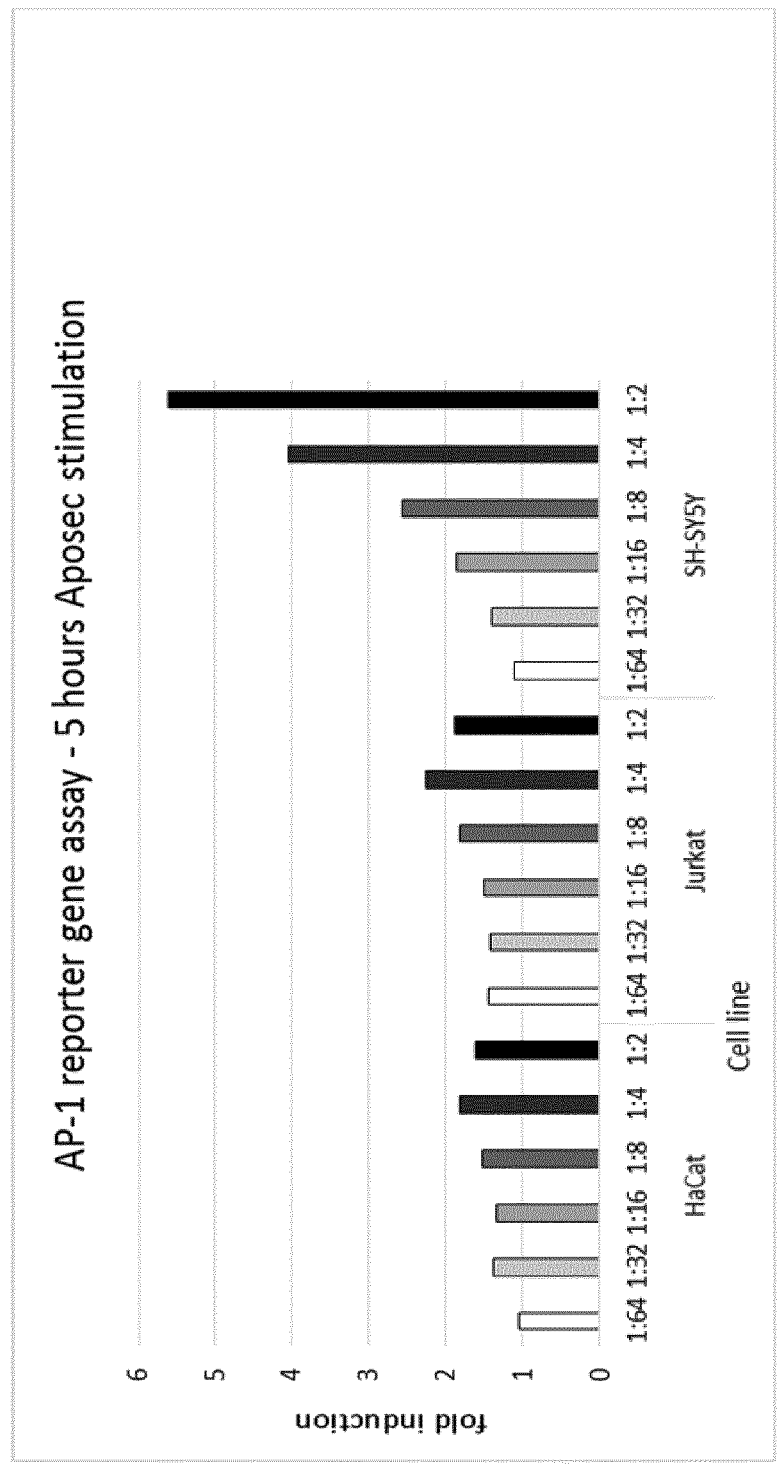

The AP-1 reporter signal is expressed relative to the cell line specific basal signal (fold induction). A dose dependent AP-1 stimulation can be observed upon 25 hours in Ha-Cat, Jurkat and SH-SY5Y cells. Upon 5 hours, a prominent AP-1 induction can only be observed in SH-SY5Y cells (see FIG. 6).

4.2 AP-1 RGA Assay 2

In this part of example 4 it is evaluated whether an overnight or e.g. a 4 hours stimulation period with Aposec can be used in a potency assay and which Aposec dose range shall be used.

SH-SY5Y AP-1 RGA cells were treated either overnight or for 4 hours with a wide dose range of Aposec. A dose range of 12 different dilutions, ranging from 1:2 to 1:47.5, was tested in a 4 hours and an overnight stimulation.

Figure 7:
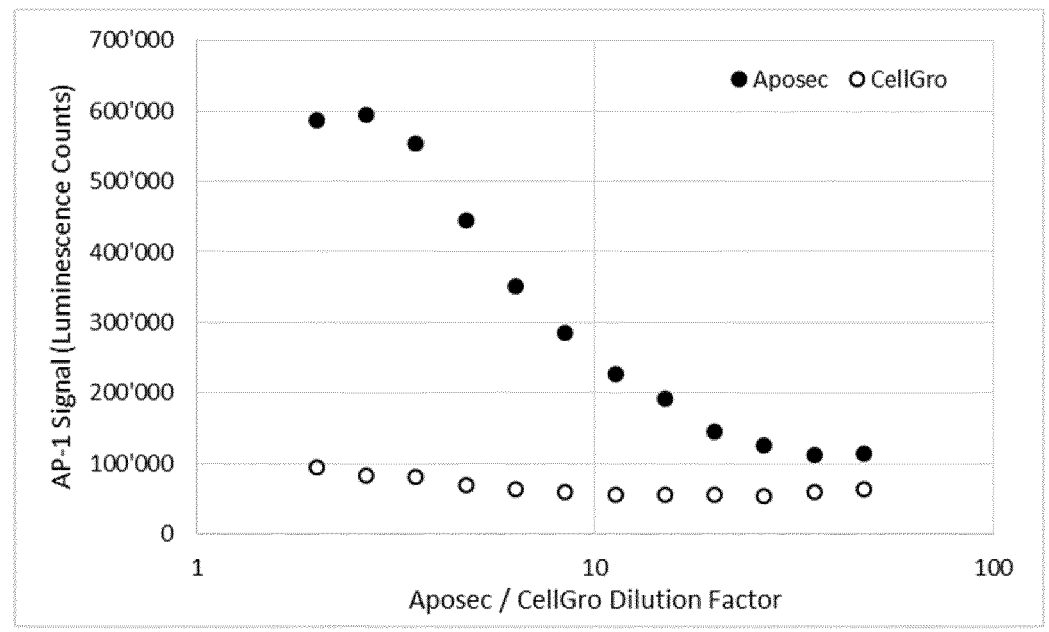
FIG. 7 shows a time and dose dependence of the AP-1 RGA assay.
Figure 7:
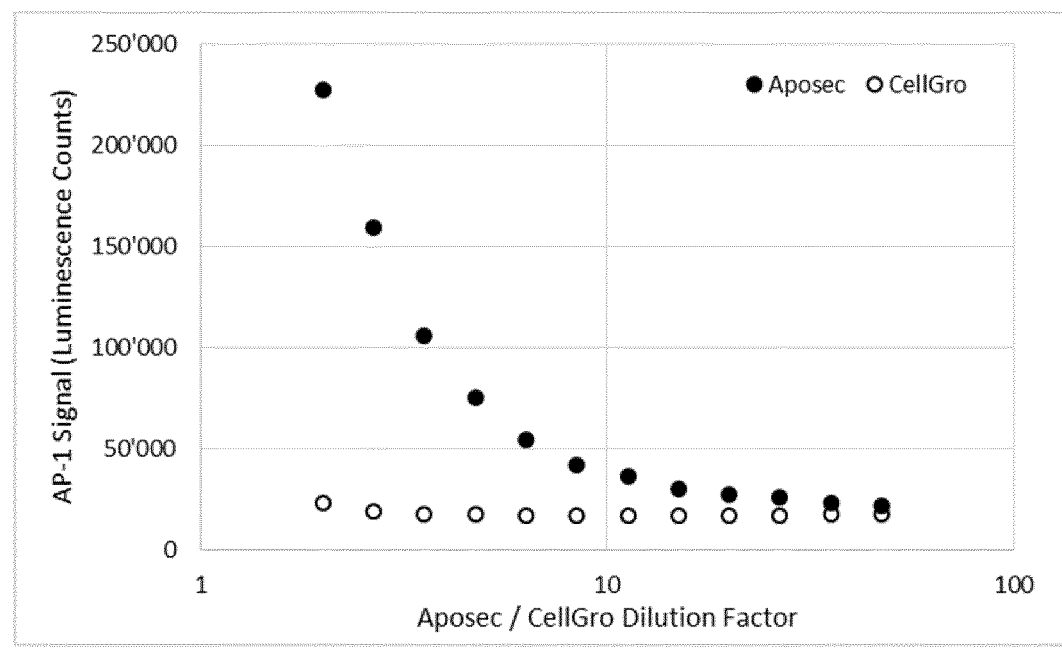

The AP-1 reporter signal (raw data=luminescence counts) are shown in FIG. 7, with a logarithmic x-axis. The 4 hours stimulation shows a preferable dose-response pattern with a plateau-like situation for the highest Aposec concentrations an almost linear pattern for the intermediate Aposec concentrations. No CellGro dependent induction can be observed at both time points.

4.3 AP-1 RGA Assay 3

In this part of example 4 it was investigated which as-say range for Aposec can be quantified with the AP-1 RGA as-say.

25%, 50% and 200% Aposec and 100% CellGro samples were used to treat AP-1 SH-SY5Y cells for 4 hours and the data was analyzed in PLA using a 4PL full curve model.

Figure 8:
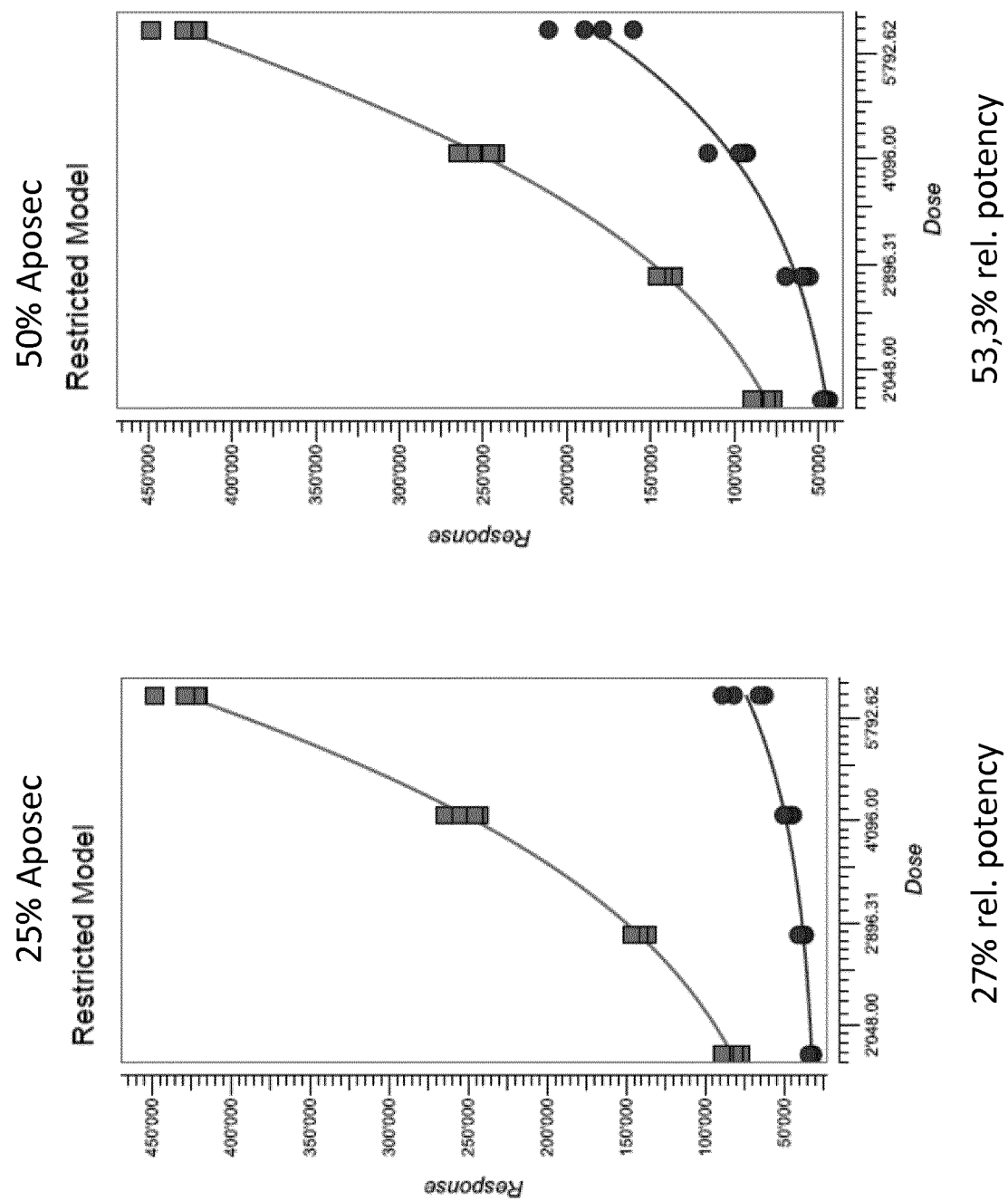
FIG. 8 shows the relative potency of various concentrations of Aposec in relation to 100% CellGro medium using an phosphorylated AP-1 RGA assay as described in example 3.
Figure 8:
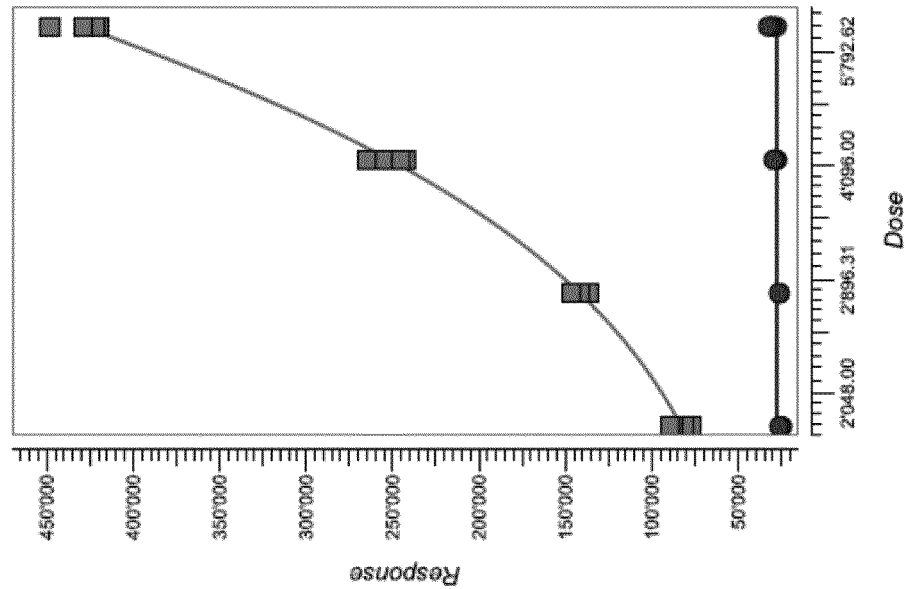
Figure 8:
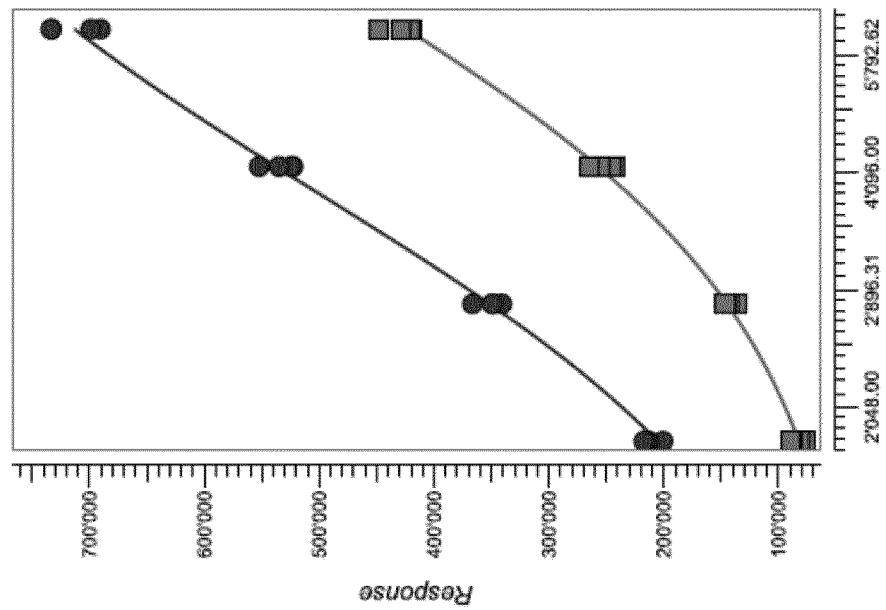

The PLA fitted curves are shown in FIG. 8 and the re-sulting relative potencies are written below the graphs.

The assay allows to quantify Aposec relative potencies from 25% to 200%. The relative potency of CellGro is in the range of 20%. This CellGro activity reflects an unspecific effect caused by the reconstitution of the lyophilisate with 0.9% NaCl (see FIG. 8).

Example 5: NF-KB Reporter Gene Assay

In this example it is evaluated whether Aposec does in-duce the NF-KB (i.e. NF-κB; nuclear factor 'kappa-light-chain-enhancer' of activated B-cells) promoter in vitro.

NF-KB RGA cells were generated using lentiviral particles (QIAGEN Order No. CLS-013L) as described above for AP-1 RGA cells. NF-KB RGA cells are stimulated with different amounts of Aposec. If Aposec stimulates the NF-KB promoter, firefly luciferase is expressed from a stably integrated expression cassette that encodes firefly luciferase under the transcriptional control by an NF-KB (nuclear factor 'kappa-light-chain-enhancer' of activated B-cells) dependent promoter. At the end of the stimulation period with APOSEC, the cells are lysed, and luciferase activity is determined using a glow-type luciferase reagent.

5.1 NF-κB RGA Assay 1

In this part of example 5 it is evaluated whether A549 NF-kB RGA cells show a dose-dependent responsiveness to Aposec stimulation.

A549 NF-kB RGA cells were stimulated for 4 hrs with different dilutions of Aposec and CellGro (both reconstituted in NaCl), before the NF-kB RGA signal was read out.

Figure 9:
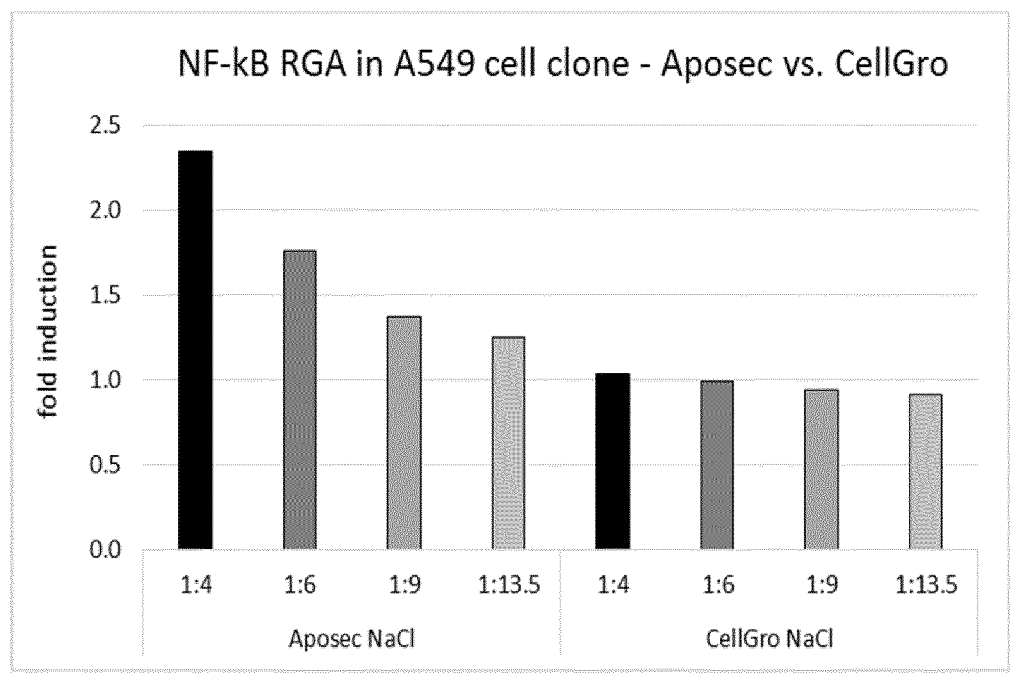
FIG. 9 shows a comparison of the induction of the NF-kB promoter using Aposec and CellGro medium.

The NF-KB reporter signal is expressed relative to the cell clone specific basal signal (fold induction). A dose dependent NF-KB stimulation can be observed upon 4 hrs stimulation, while no CellGro dependent induction can be observed (see FIG. 9).

5.2 NF-KB RGA Assay 2

In this part of example 5 the assay range for Aposec is determined with the NF-KB RGA assay.

25%, 50% and 200% Aposec and 100% CellGro samples were used to treat NF-KB A549 cells for 4 hours and the data was analyzed in PLA using a 4PL full curve mode.

Figure 10:
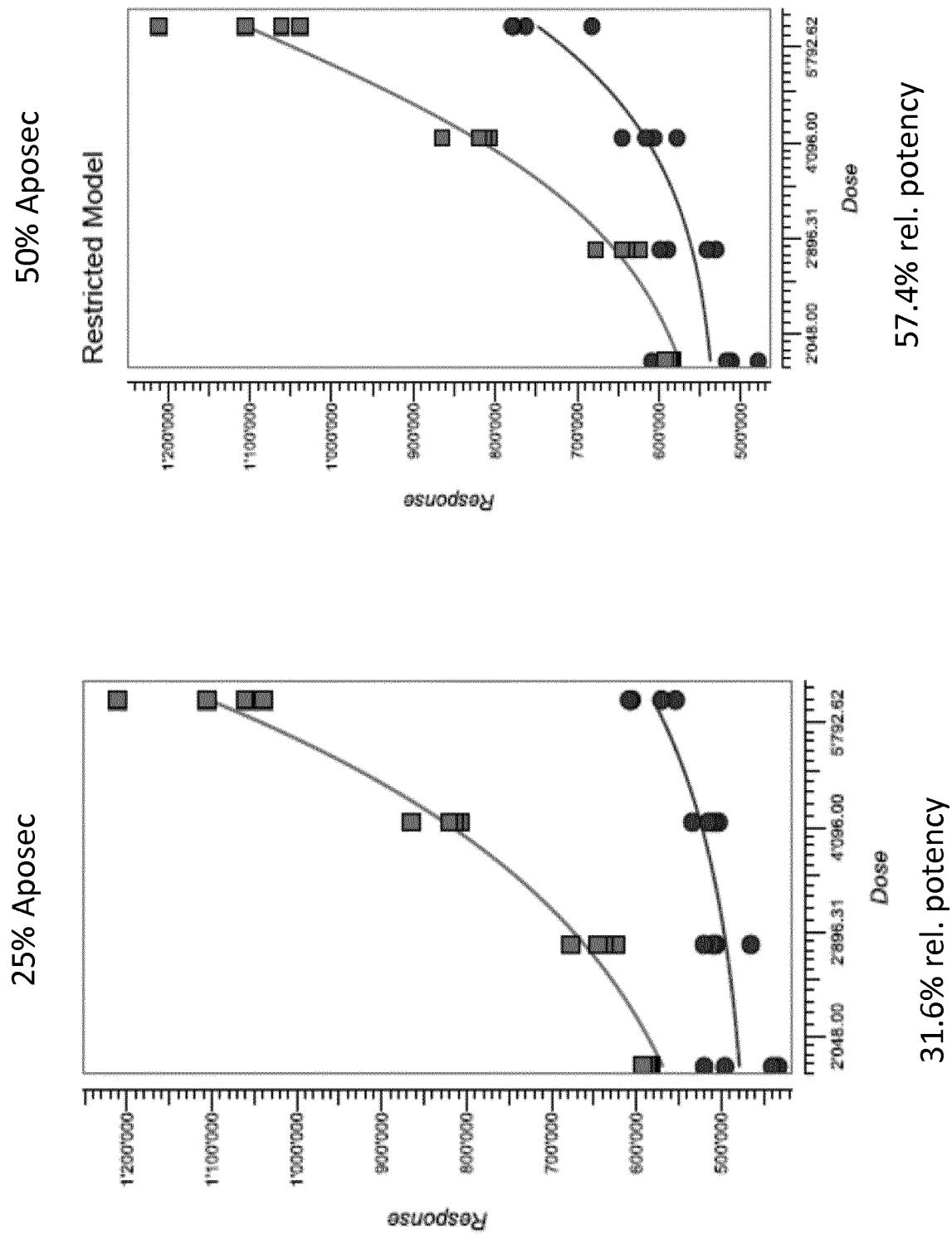
FIG. 10 shows the relative potency of various concentrations of Aposec in relation to 100% CellGro medium using an NF-kB RGA assay as described in example 5.
Figure 10:
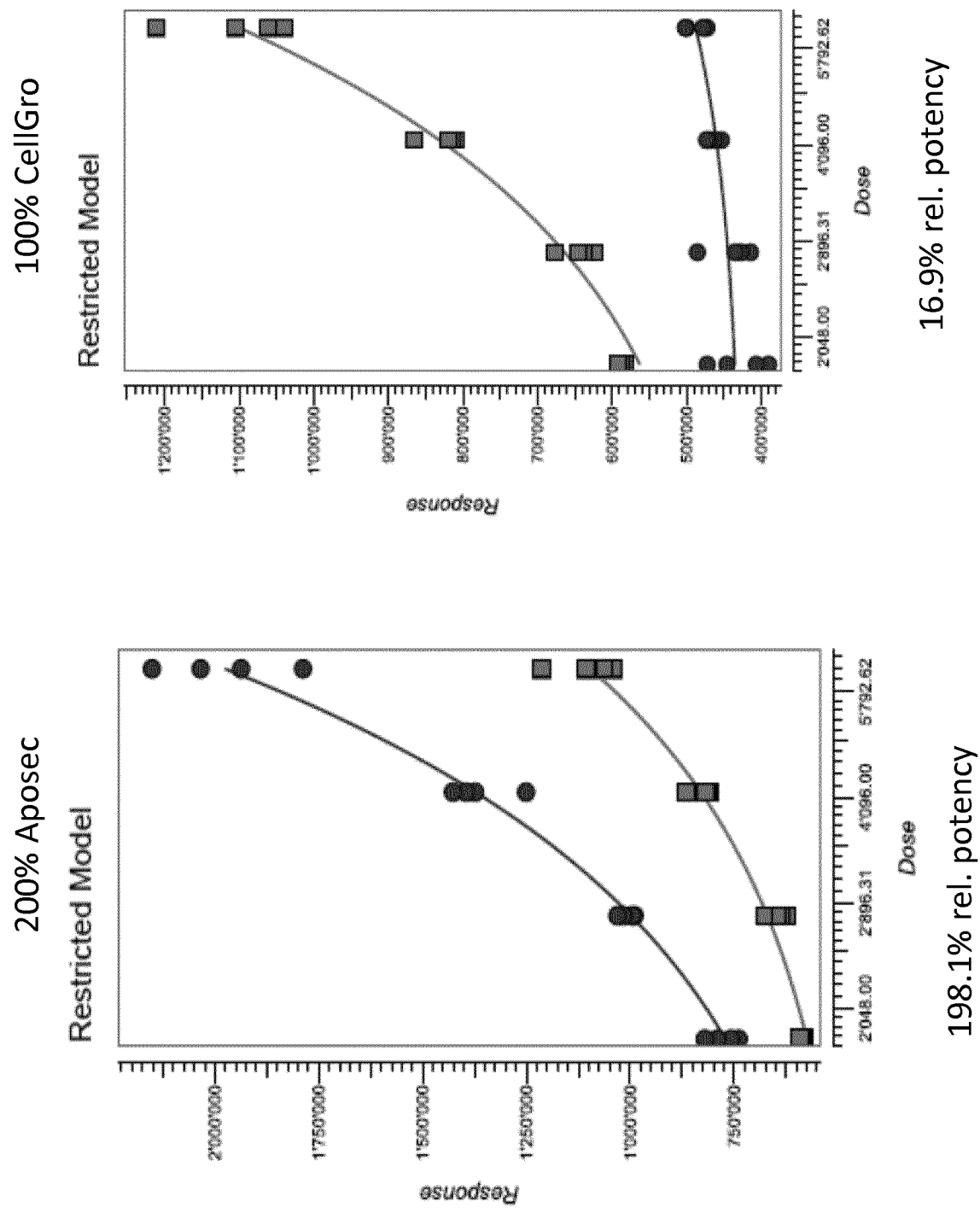

The PLA fitted curves are shown below and the resulting relative potencies are written in FIG. 10).

Example 6: APOSEC NFkB Reporter Gene Assay

The APOSEC potency can be determined via its ability to activate the NF-kB promoter in A549 cells (adenocarcinomic human alveolar basal epithelial cell line). In detail, the stimulation of the NF-kB RGA A549 cells with pre-defined amounts of APOSEC leads to the expression of firefly luciferase from a stably integrated expression cassette that encodes firefly luciferase under the transcriptional control by an NF-kB (nuclear factor 'kappa-light-chain-enhancer') dependent promoter.

The cells were cultivated in DMEM/F12+Glutamax+10% FBS+Puromycin. 20'000 cells per well were seeded in 50 µL stimulation medium (OptiMEM+Glutamax+5% FBS) to each well of the assay plate. The assay plate was incubated overnight in a humidified CO2 incubator at 37° C. Various concentrations of the APOSEC working standard (R) and test samples (A, B, C and D) were prepared in a dilution plate in assay medium. In detail, the samples were pre-diluted to 12.5 U/mL with stimulation medium: e.g. add 500 µL sample (25 U/mL) to 500 µL stimulation medium. After the transfer of 50 µL APOSEC from the dilution plate into the assay plate, final assay concentrations were: 6.25 (#1), 4.17 (#2), 2.78 (#3) and 1.85 (#4) U/mL. Upon 4 hrs stimulation with APOSEC, the cells were lysed, and luciferase activity is determined using a glow-type luciferase reagent.

The functional activity of APOSEC test samples was determined by comparison with a defined batch of APOSEC, used as reference material, analyzed in the same assay. The test samples were normalized on the basis of PMBC number used for the production of APOSEC. Relative potency was then calculated using PLA software.

Example 7: Signal Transduction Reporter Array

In this example it was evaluated whether Aposec does specifically induce certain signaling pathways.

The 'Cignal 45-Pathway Reporter Array' (Qiagen order no. CCA-901L) was used to identify signaling pathways that are specifically induced upon Aposec stimulation. The reporter pathway allows the parallel analysis of 45 different reporter gene constructs upon transient transfection of the selected cell line.

7.1 Transfection Efficacy Test 1 & 2

A549, HEK293 and HaCat cells were transfected using a control luciferase vector (Cignal Positive Control (luc), QIAGEN Order No. 336881), comparable to the luciferase vectors present in the reporter array, together with 2 different transfection reagents (Attractene (QIAGEN Order No. 301005) and Fugene HD (PROMEGA Order No. E2311)). Different DNA:transfection reagent ratios were evaluated on 2 different cell numbers per cell line (20'000 and 80'000 cells/well).

The transfection efficacy and robustness showed good results for Fugene HD which were slightly higher compared to Attractene (overall higher luminescence counts for Fugene). The luminescence counts for the HaCat cells was lower compared to HEK293 and A549 cells. HaCat cells are known to be difficult to transfect (see FIG. 11).

A second transfection efficacy test was carried out only for HEK293 and A549 cells. Fugene HD and Attractene reagents were used again. Beside the transfection efficacy (fire-fly and renilla luciferase counts), the viability of the cells was analyzed using CellTiterGlo, to exclude a negative effect on the cell viability due to the transfection. The initial results regarding the transfection efficacy could be reproduced and no obvious effect on the cell viability could be observed. Based on these results, Fugene HD with a 'Fugene to DNA' ratio of 3.375 was selected to be used in the upcoming reporter array experiments.

7.2 Signal Transduction Reporter Array—Assay 1

In this part of example 7 it was investigated which signaling pathways (reporter gene constructs) are activated specifically upon Aposec overnight stimulation in A549 and HEK293 cells.

The above described 'Cignal 45-Pathway Reporter Array' was used in HEK293 and A549 cells with 20'000 cells/well, with Fugene HD and an overnight stimulation. The cells were stimulated with Aposec (1:4 dilution or 6.25 U/mL). CellGro (1:4 dilution or 6.25 U/mL) was used as control stimulation. The used Aposec and CellGro, were both reconstituted in 0.9% NaCl.

Figure 12:
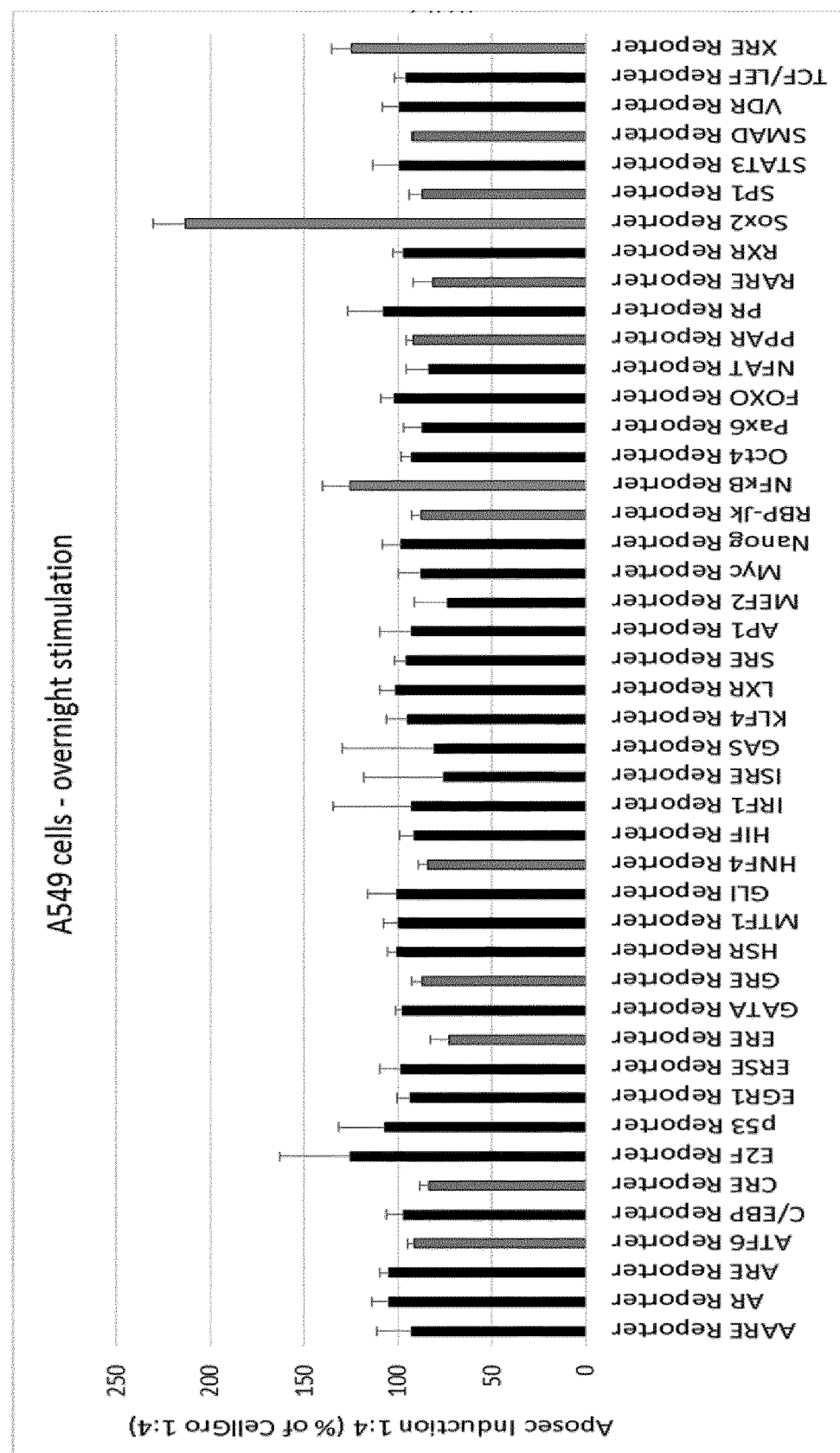
FIG. 12 shows the results of the signal transduction reporter array of example 7.2.
Figure 12:
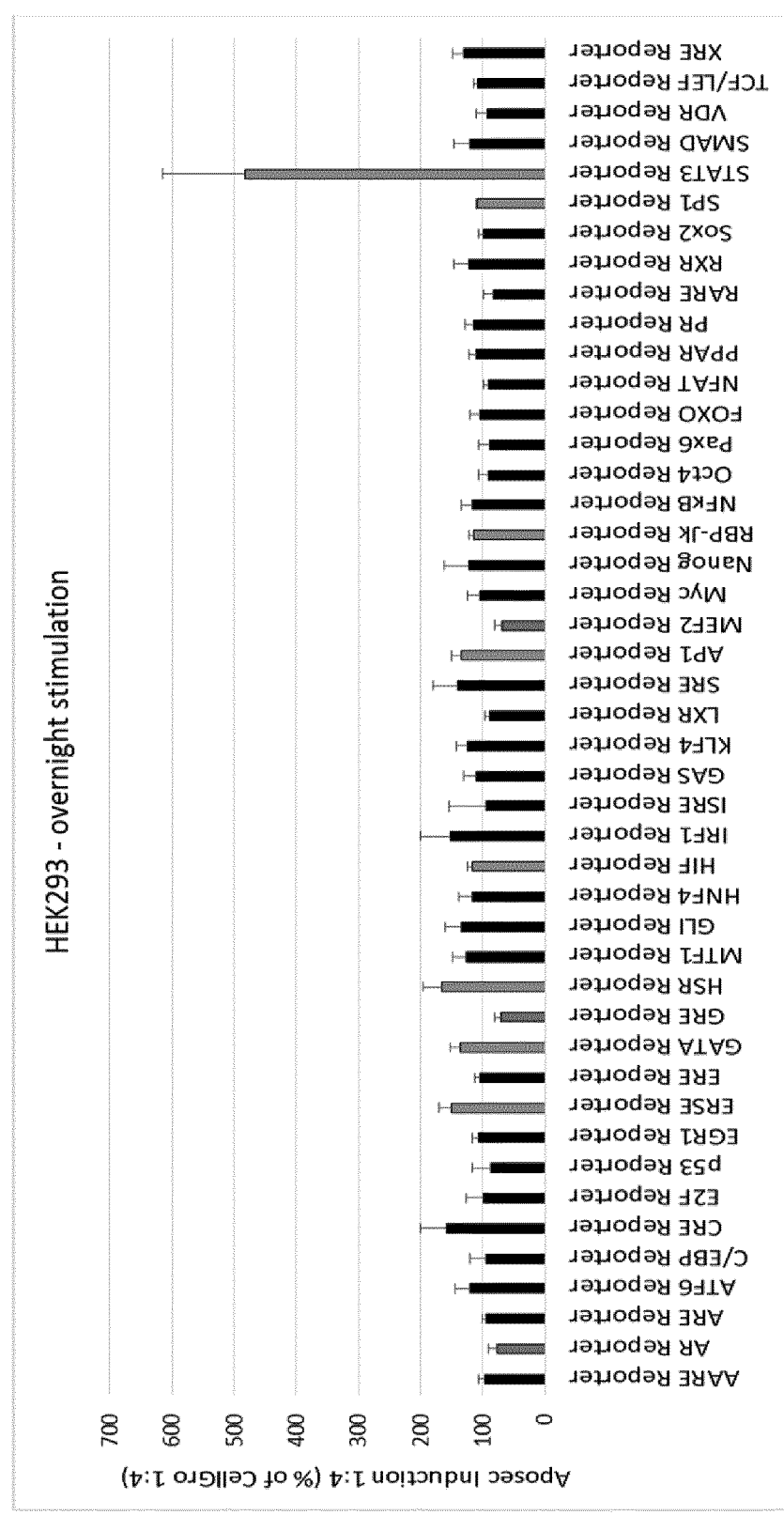
Figure 13:
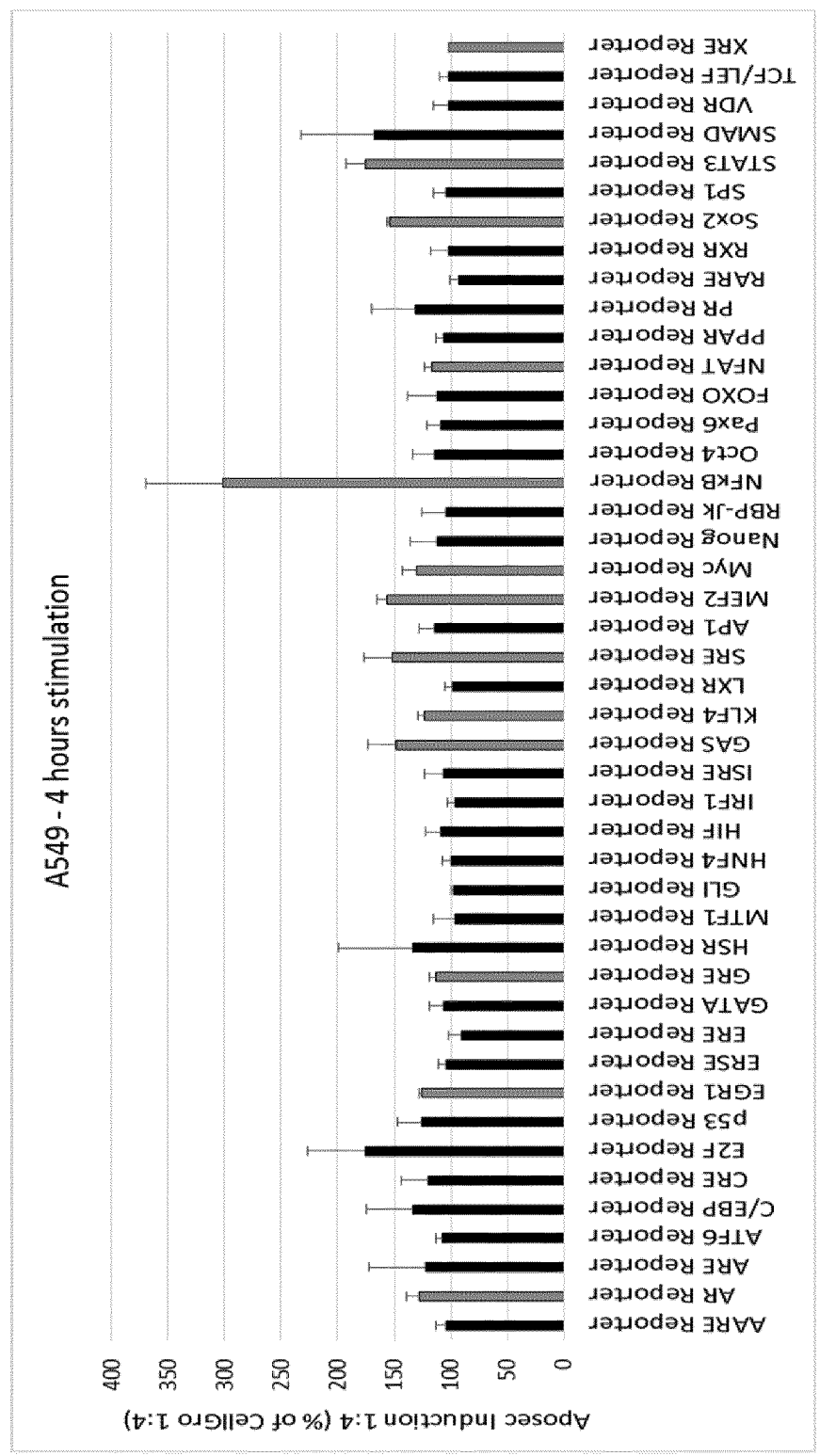
FIG. 13 shows results of the signal transduction reporter array of example 7.3.
Figure 13:
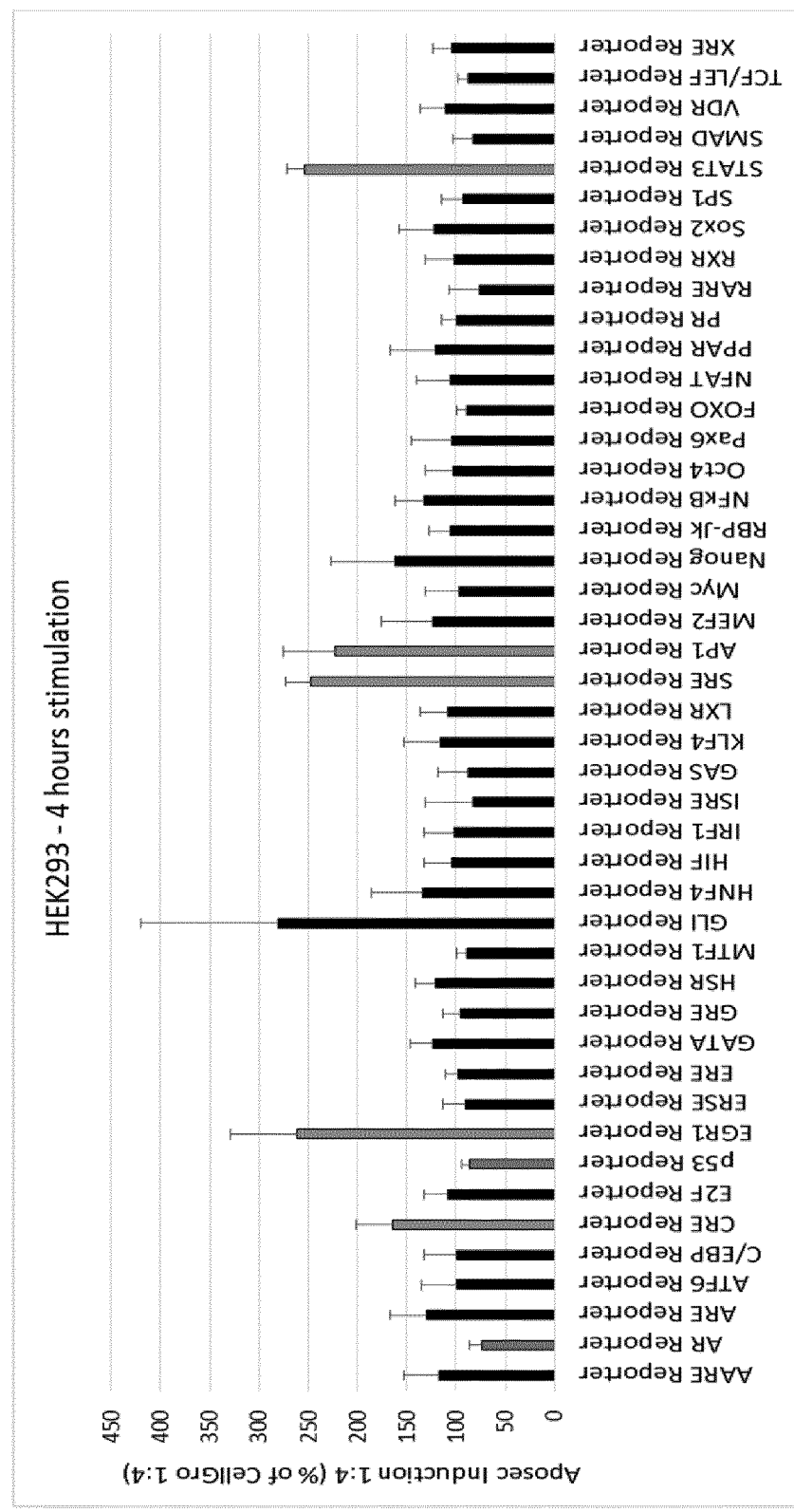

The reporter gene activities were normalized against the CellGro controls and the luminescence counts were normalized for the transfection efficacy (firefly/renilla counts). Some reporter genes/pathways have been significantly upregulated (e.g. Stat3, Sox2, NF-kB, XRE), other significantly down-regulated (e.g. RARE, ERE, MEF2) (see FIG. 12).

7.3 Signal Transduction Reporter Array—Assay 2

In this part of example 7 it was investigated which signaling pathways (reporter gene constructs) are activated specifically upon Aposec 4 hours stimulation in A549 and HEK293 cells.

The above described assay (see 7.2), in which the cells were stimulated overnight, was repeated with a 4 hours Aposec stimulation.

The reporter gene activities were normalized against the CellGro controls and the luminescence counts were normalized for the transfection efficacy (firefly/renilla counts). Some reporter genes/pathways have been significantly upregulated others significantly down-regulated.

The results of the above described reporter gene array assays seem to be robust, as the standard deviations are rather small and most of the genes are not up- or down-regulated. Furthermore, the some of the up- or down-regulated reporter genes/pathways were found in more than one assay, e.g. NF-kB, AP-1, STAT3 and Sox-2.

Example 8: Porcine Burn Model

In order to evaluate whether the secretome of PBMC cultures show a therapeutic effect comparable to a standard APOSEC preparation according to example 1 whose therapeutic efficacy has already been tested, four different PBMC supernatant preparation have been prepared following the protocol of example 1. The PBMCs used to obtain said four supernatants (A, B, C and D) have been isolated from four different individuals. As a therapeutic model a porcine burn model has been used which is extensively described in Hacker S et al. (Sci Rep 6(2016):25168).

In a first step the experiments described in examples 3.3, 4.2 and 5.1 have been repeated with the aforementioned standard APOSEC preparation and the four supernatants A, B, C and D. The amount of phosphoSer15-Hsp27 was measured after 60 min incubation and the signal of the AP-1 and NF-kB reporter activity was determined after 4 hours. It turned out that supernatants A and D showed a variation in regard to phosphoSer15-Hsp27 levels and AP-1 and NF-kB activity compared to APOSEC of less than 5%. Supernatants B and C were at approx. 35% and 50%, respectively, lower in regard to phosphoSer15-Hsp27 levels and AP-1 and NF-kB activity compared to APOSEC.

All four supernatants A, B, C and D as well as APOSEC have been combined with hydrogel in order to form a composition which can be applied on a wound. The method to obtain these preparations is described in Hacker S et al. The wounds on porcine skin have also been prepared as described in Hacker S et al. In contrast to Hacker S et al. in the present example only the mean epidermal thickness in wounds treated with APOSEC and the four supernatants was evaluated. It turned out that APOSEC and supernatants A and D showed a comparable mean epidermal thickness (125.1±23.8 µm). In contrast thereto, the application of preparations comprising supernatants B and C resulted in an epidermal thickness of 97.6±23.8 µm and 92.6±18.6 µm, respectively, which was slightly higher com-pared to a preparation comprising CellGro medium alone (88.3±14.2 µm).

The invention claimed is:

1. A method for determining potential of a supernatant of a mammalian cell culture to be used in treatment of an inflammatory condition comprising steps of
   a) incubating SH-SY5Y cells in a culture medium comprising or consisting of said supernatant,
   b) measuring a promoter activity of an activator protein 1 (AP-1) promoter, wherein the supernatant of the mammalian cell culture has the potential to be used in the treatment of the inflammatory condition, if the promoter activity of the AP-1 promoter is at least 50% higher compared to the AP-1 promoter activity measured when the SH-SY5Y cells are cultivated in a culture medium lacking said supernatant.

2. The method according to claim 1, wherein the supernatant of a mammalian cell culture is a supernatant of a peripheral blood mononuclear cell (PB MC) culture.

3. The method according to claim 1, wherein the inflammatory condition is a condition associated with ischemia, a skin condition, or an internal inflammatory condition.

4. The method according to claim 1, wherein the SH-SY5Y cells of step a) are incubated in the cell culture medium for at least 2 hours.

5. The method according to claim 4, wherein the SH-SY5Y cells of step a) are incubated in the cell culture medium for at least 4 hours, or at least 6 hours, or at least 12 hours, or at least 18 hours, or at least 24 hours.

6. The method according to claim 1, wherein the culture medium comprises at least 20% of said supernatant.

7. The method according to claim 6, wherein the culture medium comprises at least 50%, or at least 70%, or at least 80%, or at least 90%, or at least 95%, of said supernatant.

8. The method according to claim 1, wherein the culture medium of step a) is a Dulbecco's Modified Eagle Medium (DMEM), a Ham's F12 Medium (F12), a Minimum Essential Medium or a combination of one or more of these media.

9. The method according to claim 1, wherein the culture medium of step a) comprises 2 to 20% fetal bovine serum (FBS) and/or L-alanyl-L-glutamine.

10. The method according to claim 9, wherein the culture medium of step a) comprises 5 to 15% fetal bovine serum (FBS).

11. The method according to claim 1, wherein the SH-SY5Y cells comprise at least one expression cassette comprising an AP-1 promoter operably linked to at least one nucleic acid molecule encoding for a reporter protein.

12. The method according to claim 11, wherein the reporter protein is selected from the group consisting of a luciferase and a fluorescent protein.

13. The method according to claim 12, wherein the luciferase is a firefly luciferase and the fluorescent protein is a green fluorescent protein.

14. The method according to claim 1, wherein the promoter activity of the AP-1 promoter is at least 80% higher compared to the promoter activity measured when the SH-SY5Y cells are cultivated in a culture medium lacking said supernatant.

15. The method according to claim 14, wherein the promoter activity of the AP-1 promoter is at least 100% higher compared to the promoter activity measured when the SH-SY5Y cells are cultivated in a culture medium lacking said supernatant.

16. The method according to claim 14, wherein the promoter activity of the AP-1 promoter is at least 150% higher compared to the promoter activity measured when the SH-SY5Y cells are cultivated in a culture medium lacking said supernatant.

17. The method according to claim 14, wherein the promoter activity of the AP-1 promoter is at least 200%, higher compared to the promoter activity measured when the SH-SY5Y cells are cultivated in a culture medium lacking said supernatant.

18. A method for determining potential of a supernatant of a mammalian cell culture to be used in treatment of an inflammatory condition comprising steps of
   a) incubating SH-SY5Y cells in a culture medium comprising or consisting of said supernatant,
   b) measuring a promoter activity of an activator protein 1 (AP-1) promoter, wherein the supernatant of the mammalian cell culture has the potential to be used in the treatment of the inflammatory condition, if the promoter activity of the AP-1 promoter is up to 10% higher or lower compared to the promoter activity measured when the SH-SY5Y cells are cultivated in a culture medium comprising a reference supernatant of mammalian cells known to be effective for the treatment of the inflammatory condition.

19. The method according to claim 18, wherein the supernatant of a mammalian cell culture is a supernatant of a peripheral blood mononuclear cell (PBMC) culture.

20. The method according to claim 18, wherein the inflammatory condition is a condition associated with ischemia, a skin condition, or an internal inflammatory condition.

* * * * *